United States Patent
Disney et al.

(10) Patent No.: US 9,933,419 B2
(45) Date of Patent: Apr. 3, 2018

(54) SPECIFIC TARGETING OF RNA EXPANDED REPEAT SEQUENCES

(71) Applicant: THE SCRIPPS RESEARCH INSTITUTE, La Jolla, CA (US)

(72) Inventors: Matthew D. Disney, Jupiter, FL (US); Lirui Guan, Rockville, MD (US); Wang-Yong Yang, Palm Beach Gardens, FL (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 15/427,288

(22) Filed: Feb. 8, 2017

(65) Prior Publication Data

US 2017/0234859 A1 Aug. 17, 2017

Related U.S. Application Data

(63) Continuation of application No. 14/904,999, filed as application No. PCT/US2014/046626 on Jul. 15, 2014, now Pat. No. 9,586,944.

(60) Provisional application No. 61/846,204, filed on Jul. 15, 2013.

(51) Int. Cl.
*A61K 48/00* (2006.01)
*G01N 33/53* (2006.01)

(52) U.S. Cl.
CPC ..... *G01N 33/5308* (2013.01); *G01N 2500/04* (2013.01); *G01N 2500/10* (2013.01)

(58) Field of Classification Search
None
See application file for complete search history.

(56) References Cited

PUBLICATIONS

Childs-Disney, Jessica L. Rationally Designed Small Molecules Targeting the RNA That Causes Myotonic Dystrophy Type 1 Are Potently Bioactive. ACS Chem. Biol. May 18, 2012; 7(5): 856-862.*

* cited by examiner

*Primary Examiner* — Samantha Shterengarts
(74) *Attorney, Agent, or Firm* — Geoffrey K. Cooper; Thomas Fitting

(57) ABSTRACT

The present invention provides small molecule compounds that can form covalent adducts with specific sequences of RNA, such as the hairpin loop r(CUG)$^{exp}$ sequence which is a cause of myotonic dystrophy type 1 (DM1), or the r(CGG)$^{exp}$ sequence which is a cause of fragile X-associated tremor/ataxia syndrome (FXTAS); to methods of making the small molecule compounds; and to methods of using the small molecular compounds in the treatment of DM1 or of FXTAS in patients afflicted therewith. The invention further provides a method for identifying an RNA target of a small molecule drug in vivo, using a small molecule drug conjugated to an RNA-reactive crosslinker group and a reporter group, contacting a cell or nucleic acid extract with the small molecule drug conjugate, then separating RNA targets crosslinked to the small molecule drug conjugate by interaction of the affinity group with a complementary affinity group.

7 Claims, 18 Drawing Sheets

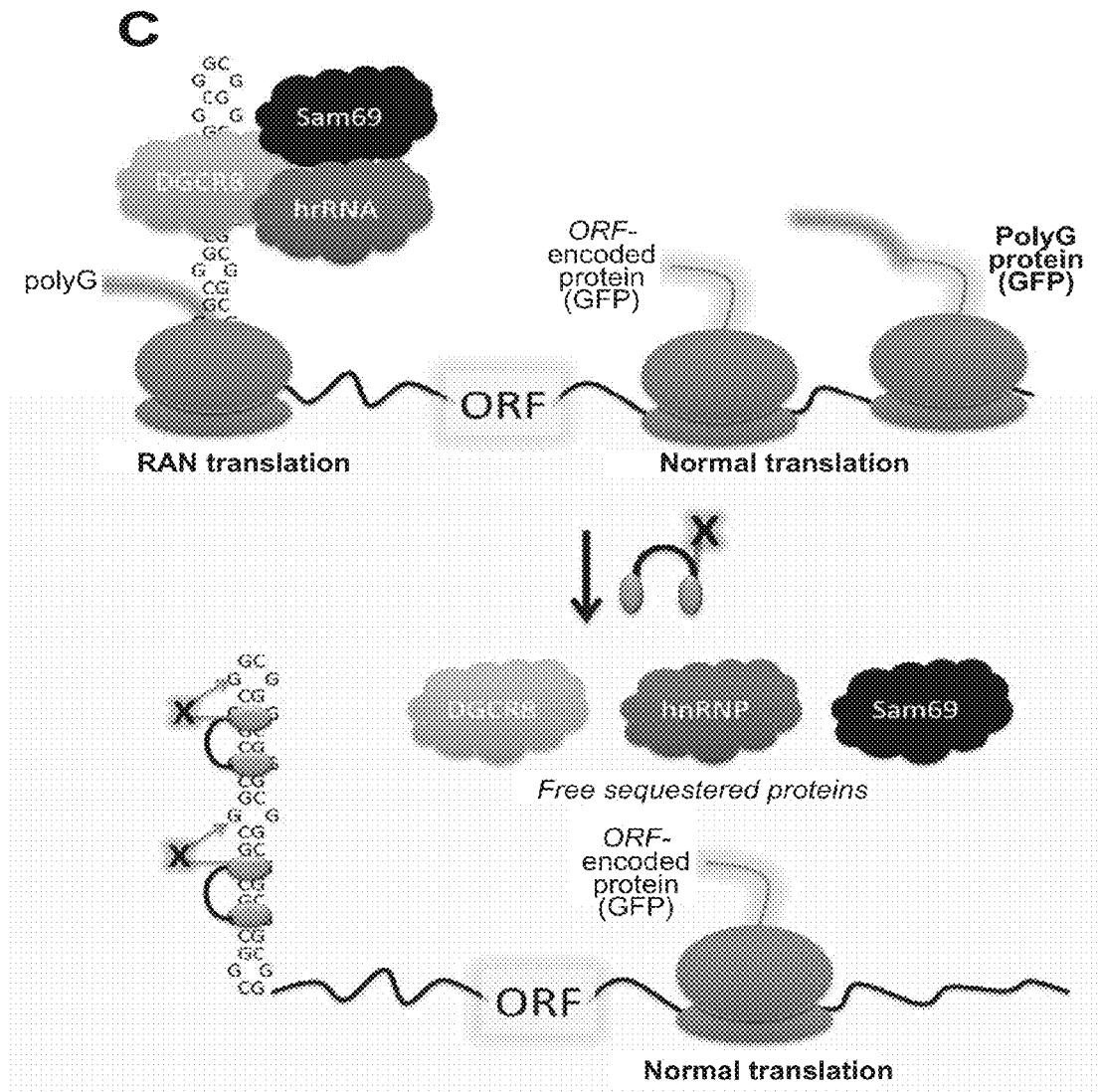

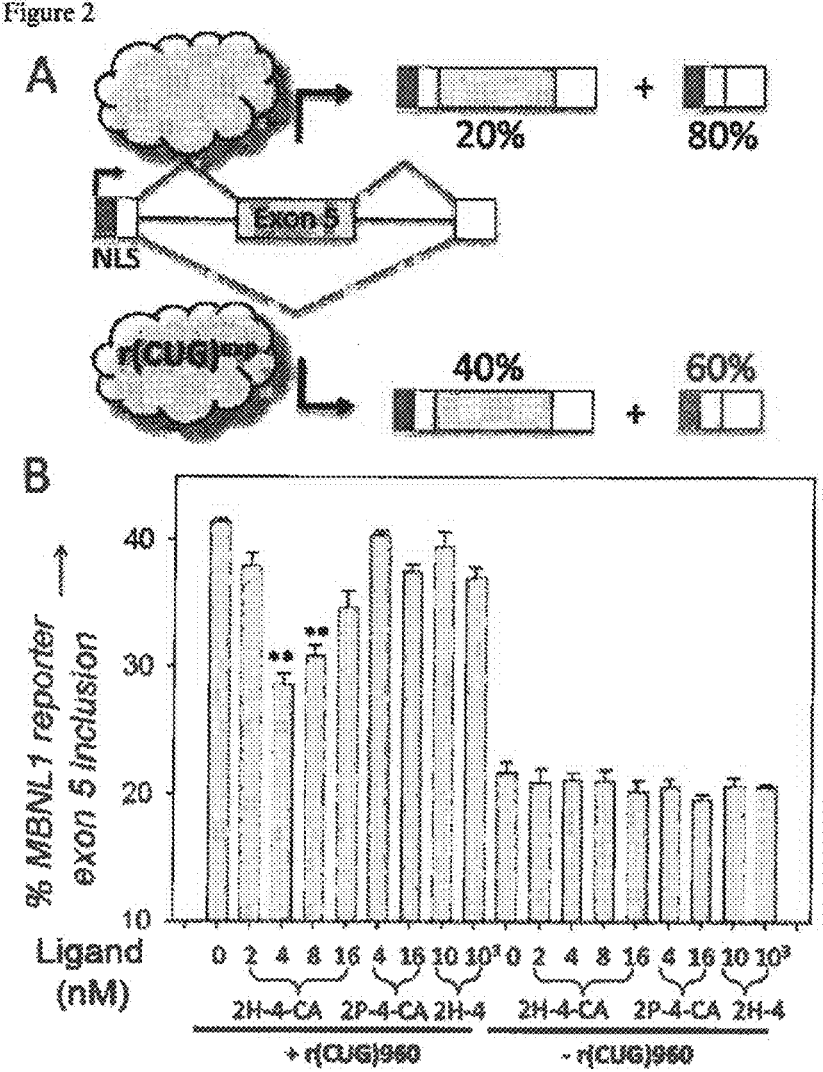

Figure 15
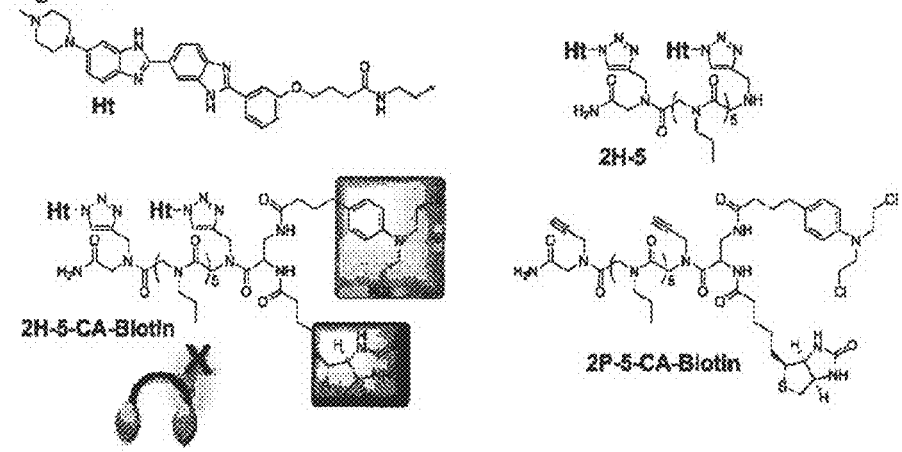
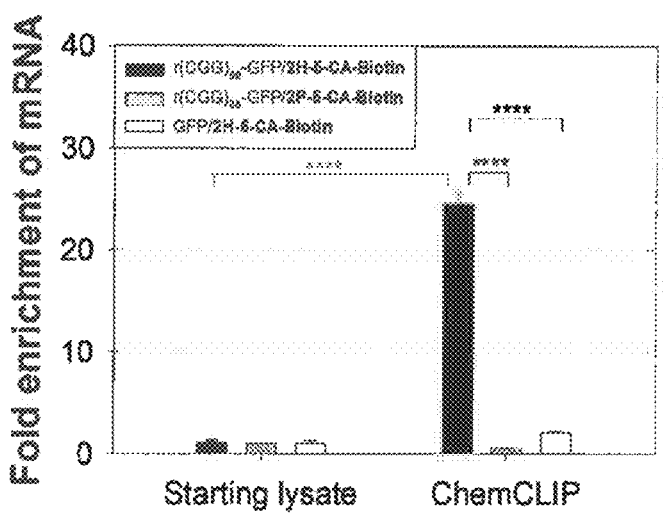

SEQUENCE LISTING

<160> NUMBER OF SEQ ID NOS: 5

<210> SEQ ID NO 1
<211> LENGTH: 2880
<212> TYPE: RNA
<213> ORGANISM: Artificial sequence
<220> FEATURE:
<223> OTHER INFORMATION: synthetic sequence

<400> SEQUENCE: 1

| | |
|---|---:|
| cugcugcugc ugcugcugcu gcugcugcug cugcugcugc ugcugcugcu gcugcugcug | 60 |
| cugcugcugc ugcugcugcu gcugcugcug cugcugcugc ugcugcugcu gcugcugcug | 120 |
| cugcugcugc ugcugcugcu gcugcugcug cugcugcugc ugcugcugcu gcugcugcug | 180 |
| cugcugcugc ugcugcugcu gcugcugcug cugcugcugc ugcugcugcu gcugcugcug | 240 |
| cugcugcugc ugcugcugcu gcugcugcug cugcugcugc ugcugcugcu gcugcugcug | 300 |
| cugcugcugc ugcugcugcu gcugcugcug cugcugcugc ugcugcugcu gcugcugcug | 360 |
| cugcugcugc ugcugcugcu gcugcugcug cugcugcugc ugcugcugcu gcugcugcug | 420 |
| cugcugcugc ugcugcugcu gcugcugcug cugcugcugc ugcugcugcu gcugcugcug | 480 |
| cugcugcugc ugcugcugcu gcugcugcug cugcugcugc ugcugcugcu gcugcugcug | 540 |
| cugcugcugc ugcugcugcu gcugcugcug cugcugcugc ugcugcugcu gcugcugcug | 600 |
| cugcugcugc ugcugcugcu gcugcugcug cugcugcugc ugcugcugcu gcugcugcug | 660 |
| cugcugcugc ugcugcugcu gcugcugcug cugcugcugc ugcugcugcu gcugcugcug | 720 |
| cugcugcugc ugcugcugcu gcugcugcug cugcugcugc ugcugcugcu gcugcugcug | 780 |
| cugcugcugc ugcugcugcu gcugcugcug cugcugcugc ugcugcugcu gcugcugcug | 840 |
| cugcugcugc ugcugcugcu gcugcugcug cugcugcugc ugcugcugcu gcugcugcug | 900 |
| cugcugcugc ugcugcugcu gcugcugcug cugcugcugc ugcugcugcu gcugcugcug | 960 |
| cugcugcugc ugcugcugcu gcugcugcug cugcugcugc ugcugcugcu gcugcugcug | 1020 |
| cugcugcugc ugcugcugcu gcugcugcug cugcugcugc ugcugcugcu gcugcugcug | 1080 |
| cugcugcugc ugcugcugcu gcugcugcug cugcugcugc ugcugcugcu gcugcugcug | 1140 |
| cugcugcugc ugcugcugcu gcugcugcug cugcugcugc ugcugcugcu gcugcugcug | 1200 |
| cugcugcugc ugcugcugcu gcugcugcug cugcugcugc ugcugcugcu gcugcugcug | 1260 |
| cugcugcugc ugcugcugcu gcugcugcug cugcugcugc ugcugcugcu gcugcugcug | 1320 |
| cugcugcugc ugcugcugcu gcugcugcug cugcugcugc ugcugcugcu gcugcugcug | 1380 |
| cugcugcugc ugcugcugcu gcugcugcug cugcugcugc ugcugcugcu gcugcugcug | 1440 |
| cugcugcugc ugcugcugcu gcugcugcug cugcugcugc ugcugcugcu gcugcugcug | 1500 |
| cugcugcugc ugcugcugcu gcugcugcug cugcugcugc ugcugcugcu gcugcugcug | 1560 |
| cugcugcugc ugcugcugcu gcugcugcug cugcugcugc ugcugcugcu gcugcugcug | 1620 |
| cugcugcugc ugcugcugcu gcugcugcug cugcugcugc ugcugcugcu gcugcugcug | 1680 |
| cugcugcugc ugcugcugcu gcugcugcug cugcugcugc ugcugcugcu gcugcugcug | 1740 |
| cugcugcugc ugcugcugcu gcugcugcug cugcugcugc ugcugcugcu gcugcugcug | 1800 |
| cugcugcugc ugcugcugcu gcugcugcug cugcugcugc ugcugcugcu gcugcugcug | 1860 |
| cugcugcugc ugcugcugcu gcugcugcug cugcugcugc ugcugcugcu gcugcugcug | 1920 |
| cugcugcugc ugcugcugcu gcugcugcug cugcugcugc ugcugcugcu gcugcugcug | 1980 |
| cugcugcugc ugcugcugcu gcugcugcug cugcugcugc ugcugcugcu gcugcugcug | 2040 |

```
cugcugcugc ugcugcugcu gcugcugcug cugcugcugc ugcugcugcu gcugcugcug      2100
cugcugcugc ugcugcugcu gcugcugcug cugcugcugc ugcugcugcu gcugcugcug      2160
cugcugcugc ugcugcugcu gcugcugcug cugcugcugc ugcugcugcu gcugcugcug      2220
cugcugcugc ugcugcugcu gcugcugcug cugcugcugc ugcugcugcu gcugcugcug      2280
cugcugcugc ugcugcugcu gcugcugcug cugcugcugc ugcugcugcu gcugcugcug      2340
cugcugcugc ugcugcugcu gcugcugcug cugcugcugc ugcugcugcu gcugcugcug      2400
cugcugcugc ugcugcugcu gcugcugcug cugcugcugc ugcugcugcu gcugcugcug      2460
cugcugcugc ugcugcugcu gcugcugcug cugcugcugc ugcugcugcu gcugcugcug      2520
cugcugcugc ugcugcugcu gcugcugcug cugcugcugc ugcugcugcu gcugcugcug      2580
cugcugcugc ugcugcugcu gcugcugcug cugcugcugc ugcugcugcu gcugcugcug      2640
cugcugcugc ugcugcugcu gcugcugcug cugcugcugc ugcugcugcu gcugcugcug      2700
cugcugcugc ugcugcugcu gcugcugcug cugcugcugc ugcugcugcu gcugcugcug      2760
cugcugcugc ugcugcugcu gcugcugcug cugcugcugc ugcugcugcu gcugcugcug      2820
cugcugcugc ugcugcugcu gcugcugcug cugcugcugc ugcugcugcu gcugcugcug      2880

<210> SEQ ID NO 2
<211> LENGTH: 30
<212> TYPE: RNA
<213> ORGANISM: Artificial sequence
<220> FEATURE:
<223> OTHER INFORMATION: synthetic sequence

<400> SEQUENCE: 2
cugcugcugc ugcugcugcu gcugcugcug                                        30

<210> SEQ ID NO 3
<211> LENGTH: 264
<212> TYPE: RNA
<213> ORGANISM: Artificial sequence
<220> FEATURE:
<223> OTHER INFORMATION: synthetic sequence

<400> SEQUENCE: 3
cggcggcggc ggcggcggcg gcggcggcgg cggcggcggc ggcggcggcg gcggcggcgg       60
cggcggcggc ggcggcggcg gcggcggcgg cggcggcggc ggcggcggcg gcggcggcgg      120
cggcggcggc ggcggcggcg gcggcggcgg cggcggcggc ggcggcggcg gcggcggcgg      180
cggcggcggc ggcggcggcg gcggcggcgg cggcggcggc ggcggcggcg gcggcggcgg      240
cggcggcggc ggcggcggcg gcgg                                             264

<210> SEQ ID NO 4
<211> LENGTH: 36
<212> TYPE: DNA
<213> ORGANISM: Artificial sequence
<220> FEATURE:
<223> OTHER INFORMATION: synthetic sequence

<400> SEQUENCE: 4
ccgccgccgc cgccgccgcc gccgccgccg ccgccg                                 36

<210> SEQ ID NO 5
<211> LENGTH: 180
<212> TYPE: RNA
<213> ORGANISM: Artificial sequence
<220> FEATURE:
```

```
<223> OTHER INFORMATION: synthetic sequence

<400> SEQUENCE: 5
cggcggcggc ggcggcggcg gcggcggcgg cggcggcggc ggcggcggcg gcggcggcgg        60
cggcggcggc ggcggcggcg gcggcggcgg cggcggcggc ggcggcggcg gcggcggcgg       120
cggcggcggc ggcggcggcg gcggcggcgg cggcggcggc ggcggcggcg gcggcggcgg       180
```

SPECIFIC TARGETING OF RNA EXPANDED REPEAT SEQUENCES

CROSS-REFERENCE TO RELATED APPLICATIONS

This application claims the priority of U.S. Ser. No. 61/846,204, filed Jul. 15, 2013, the disclosure of which is incorporated herein by reference in its entirety.

BACKGROUND

Although RNA targets in the transcriptome are numerous, there is a dearth of small molecule chemical probes that can be used to study RNA function and dysfunction. Despite great interest in this area, the development of such compounds is difficult owing to a lack of fundamental information, or design principles, that could enable the design of compounds that selectively target RNA in a cell.

One approach to design compounds that affect function is to study RNA motif-small molecule interactions, thereby identifying small molecule "modules" that bind regions of an RNA of interest. Affinity and selectivity of the modules can be improved by linking them together to bind two or more regions in the desired RNA. Indeed, such a bottom-up approach has been used to design compounds that target repeating transcripts and other RNAs.

Covalent adduct formation between small molecules and DNA has been an effective therapeutic strategy for cancer.[1] However, analogous approaches for disease-associated RNAs have been only sparsely reported.[2]

RNA is an interesting and increasingly important drug target due to its essential functions and association with various diseases. Yet, there are relatively few small molecules that target RNAs in living cells and affect function.[3] The bacterial ribosome is the most well studied target of small molecules, which have served as therapeutics and probes of ribosomal function.[4] Compounds targeting other RNAs are needed to enable similar studies, yet few have been reported.

The development of small molecule chemical probes or therapeutics that target RNA remains a significant challenge despite the great interest in such compounds. The most significant barrier to compound development is a lack of knowledge of the chemical and RNA motif spaces that interact specifically.

Myotonic dystrophy (dystrophia myotonica, myotonia atrophica) is a chronic, slowly progressing, highly variable, inherited multisystemic disease. It is characterized by wasting of the muscles (muscular dystrophy), cataracts, heart conduction defects, endocrine changes, and myotonia. Two types of myotonic dystrophy exist. Type 1 (DM1), also known as Steinert disease, has a severe congenital form and a milder childhood-onset form as well as an adult-onset form.

RNA plays diverse and important roles in biological processes, including myotonic dystrophy type 1 (DM1).[5] DM1 is caused when expanded repeats present in UTR's sequester proteins that are involved in pre-mRNA splicing regulation. Sequestration of these proteins causes the aberrant splicing of a variety of pre-mRNAs, leading to the expression of defective proteins. Thus, DM1 is caused by an RNA gain-of-function.

In addition to RNA gain-of-function, repeating transcripts can also cause disease via by their translation into toxic proteins with or without the use of a start codon.[6e] A common defect caused by the gain-of-function by expanded repeats is dysregulation of alternative pre-mRNA splicing.[7c] For example, fragile X-associated tremor/ataxia syndrome (FXTAS) is caused by an expanded r(CGG) repeat (r(CGG)$^{exp}$), which binds and sequesters various proteins including DiGeorge Syndrome Critical Region 8 protein (DGCR8), Src-associated in mitosis, 68 kDa protein (Sam68), and others.[8b,9b] Sequestration of these proteins causes deregulation of the microRNA processing and alternative pre-mRNA splicing.[8b,9b] As has been demonstrated for the RNAs that cause the myotonic dystrophies, amyotrophic lateral sclerosis, and FXTAS, expanded repeating RNAs are also translated without the use of a start codon, or repeat-associated non-ATG (RAN) translation.[10b,11b,12b] RAN translation produces toxic polymeric proteins that appear to contribute to disease.

SUMMARY

One major class of disease-causing RNAs is expanded repeating transcripts. These RNAs cause disease via multiple mechanisms, including gain-of-function, in which repeating RNAs bind and sequester proteins involved in RNA biogenesis, and repeat-associated non-ATG (RAN) translation, in which repeating transcripts are translated into toxic proteins without use of a canonical start codon.

The present invention is directed, in various embodiments, to small molecule compounds that can form covalent adducts with specific sequences of RNA, such as the hairpin loop r(CUG)$^{exp}$ sequence which is a cause of myotonic dystrophy type 1 (DM1) or the hairpin loop r(CGG)$^{exp}$ sequence which is a cause of fragile X-associated tremor/ataxia syndrome (FXTAS); to methods of making the small molecule compounds; and to methods of using the small molecular compounds to form sequence-specific covalent complexes with RNA comprising the r(CUG)$^{exp}$ sequence, such as in the treatment of DM1 in patients afflicted therewith; and to methods of using the small molecule compounds to form sequence-specific covalent complexes with RNA comprising the r(CGG)$^{exp}$ sequence, such as in the treatment of fragile X-associated tremor/ataxia syndrome (FXTAS) in patients afflicted therewith.

Additionally, in various embodiments the invention provides a method of identifying an RNA that binds small molecules in living cells by using a small molecule-enabled immunoprecipitation approach. The invention can provide a method of identifying an RNA target of a small molecule drug in vivo, comprising contacting a living cell with a small molecule drug conjugate comprising an RNA targeting group, a crosslinking group reactive with the RNA, and an affinity group, then, optionally, activating the crosslinking group, then, separating RNA targets crosslinked to the small molecule drug conjugate by an interaction of the affinity group with a complementary affinity group. Covalent adduct formation serves to identify in live cells the RNA targets of the particular small molecule of which the conjugate is formed. By using biotinylated compounds, cellular lysates can be placed over streptavidin resin and the bound RNAs identified by RNA sequencing, Northern blot, etc.

In various embodiments, the invention provides an RNA-targeting compound of formula (I)

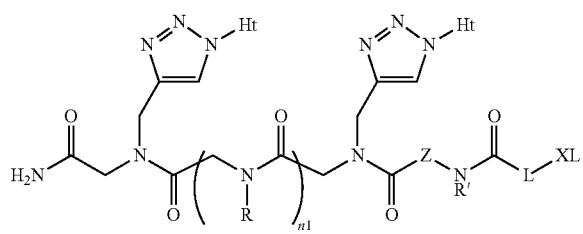

wherein
each individually selected R or R' is H or (C1-C6)alkyl;
n1 is 2, 3, 4, 5, or 6;
Z is a (C1-C3)alkylene group, optionally substituted with a reporter or affinity group;
L is a linker group comprising an optionally substituted (C1-C6)alkylene, wherein one or two carbon atoms is optionally replaced by O;
XL is an RNA-reactive crosslinking group;
each individually selected Ht is a group of formula

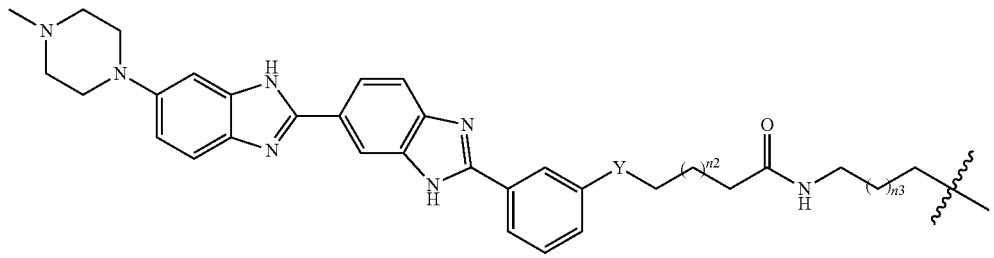

wherein
n2 is 0, 1, 2, or 3;
n3 is 0, 1, 2, or 3;
Y is O or $CH_2$;
a wavy line indicates a point of bonding;
or any tautomer thereof; or any salt thereof, or any stereoisomer thereof.

The RNA-reactive crosslinking group can be an alkylating reagent, such as a chlorambucil derivative, or can be a crosslinking group comprising a triggered crosslinker using photochemical or shape-triggered catalysis.

In various embodiments, the invention provides a covalently-linked complex of the compound of formula (I) of the invention and a segment of RNA comprising a hairpin loop $r(CUG)^{exp}$ sequence.

In various embodiments, the invention provides a covalently-linked complex of the compound of formula (I) of the invention and a segment of RNA comprising a hairpin loop $r(COG)^{exp}$ sequence.

In various embodiments, the invention provides a method of a treatment of a patient suffering from DM1, comprising administering to the patient an effective dose of a compound of invention.

In various embodiments, the invention provides a method of a treatment of a patient suffering from fragile X-associated tremor/ataxia syndrome (FXTAS), comprising administering to the patient an effective dose of a compound of invention.

In various embodiments, the invention provides a method of identifying an RNA target of a small molecule drug in vivo, comprising contacting a living cell with a small molecule drug conjugate covalently bonded to a crosslinking group reactive with the RNA and an affinity group, then, optionally, activating the crosslinking group, then, separating RNA targets crosslinked to the small molecule drug conjugate by an interaction of the affinity group with a complementary affinity group. The nucleotide sequence of the RNA targets crosslinked to the small molecule drug conjugate can then be determined. The RNA-reactive crosslinking group can be an alkylating reagent, such as a chlorambucil derivative, or can be a crosslinking group is a triggered crosslinker using photochemical or shape-triggered catalysis. The affinity group can be any group having a complementary affinity group, i.e., a group that tightly and specifically binds the affinity group, for example, biotin-streptavidin.

BRIEF DESCRIPTION OF THE FIGURES

FIG. 2 depicts: A, schematic of the MBNL1 mini-gene used to study DM1-associated pre-mRNA splicing defects that was previously described.[6c] MBNL1 protein is indicated by the cloud. B, data for the series of compounds studied showing that 2H-4-CA improves pre-mRNA splicing defects to a greater extent than do 2H-4 or 2P-4-CA. "**" indicates a statistical significance of >99% confidence.

FIG. 15 depicts the structures of the small molecule that targets r(CGG)$^{exp}$, 2H-5-CA-Biotin, and control compounds and results of ChemCLIP. Top, The 2H-5-CA-Biotin was appended with a reactive module (red box) and a biotin purification module (grey box) to improve potency and enable identification of cellular targets. 2H-5 is a non-covalent binder to r(CGG)$^{exp}$ and was described previously.[18] The 2P-5-CA-Biotin lacks RNA binding modules. Bottom, the results of ChemCLIP pull down of RNA targets in cells upon exposure to reactive compounds. Compound 2H-5-CA-Biotin had a 24-fold enrichment in the pull down of r(CGG)$_{88}$-GFP relative to starting lysate and the enrichment of this compound relative to ChemCLIP of 2H-5-CA-Biotin with cells that express only GFP or ChemCLIP of 2P-5-CA-Biotin pull down of cells expressing r(CGG)$_{88}$-GFP.

DETAILED DESCRIPTION

Overview

Figure 1:
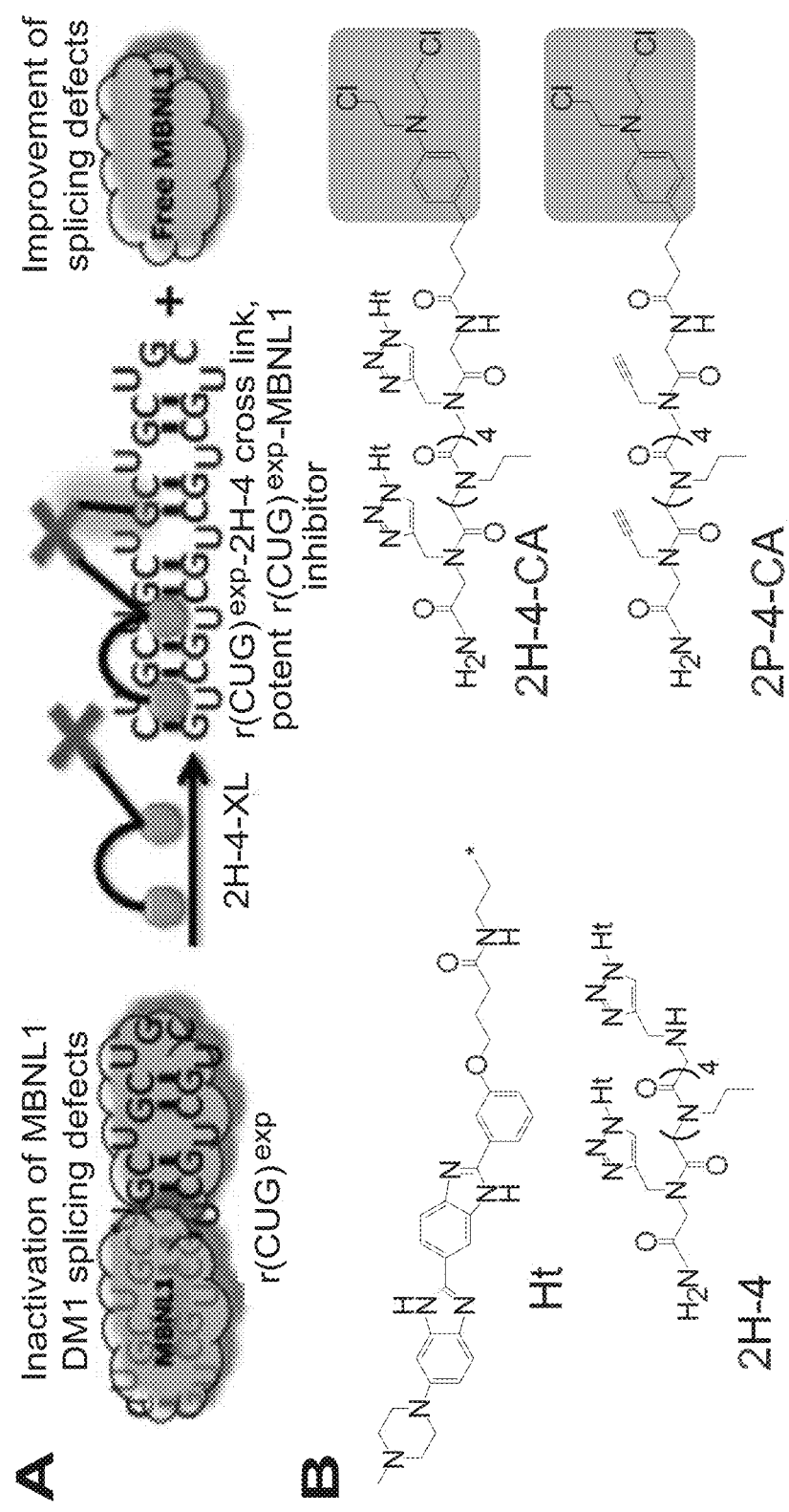
FIG. 1 shows: A, in a scheme for the $r(CUG)^{exp}$-MBNL1 interaction that contributes to DM1 and the structures of designed compounds, the $r(CUG)^{exp}$-MBNL1 complex that causes DM1. Modularly assembled small molecules targeting $r(CUG)^{exp}$ were appended with a reactive group (XL) to cross link them to the toxic transcript; B, structures of the compounds designed and tested in this study. The reactive module, a derivative of chlorambucil, is highlighted with grey boxes; C; Modes of toxicity associated with $r(CGG)^{exp}$, the causative agent of FXTAS. Top, the repeating RNA folds into a hairpin structure that binds and sequesters proteins that regulate RNA processing. Additionally, repeating transcripts are translated without a start codon in RAN translation, producing toxic polymeric proteins that contribute to pathogenesis. Bottom, small molecules that bind to and react with r(CGG)exp free bound proteins, improving defects in RNA processing and inhibiting production of RAN, but not normal, translation products.

The invention, in various embodiments, provides a programmable and potentially general approach to react small molecules with RNA in cells. Specifically, we disclose and claim a small molecule we designed that binds r(CUG)$^{exp}$, the causative agent of myotonic dystrophy type 1 (DM1), and improves DM1-associated defects in cell culture models was appended with an electrophilic, nucleic acid-reactive module (FIGS. 1A, 1B). Using this compound, we determined that: (i) covalent binding engenders an ~2500-fold improvement in potency relative to non-covalently bound analogs; (ii) damaged mRNAs are not degraded more rapidly than undamaged ones; and, (iii) RNA-small molecule interactions can be isolated and identified in a cell-wide manner, unequivocally demonstrating that the small molecules of our design can target r(CUG)$^{exp}$. These studies provide a potentially transformative foundation to manipulate and study RNA cellular function with designer small molecules.

We further disclose and claim a small molecule that binds and reacts with the expanded repeating RNA of r(CGG) in a 5'untranslated region (r(CGG)$^{exp}$), the cause of fragile X-associated tremor ataxia syndrome (FXTAS), that potently improves pre-mRNA splicing and repeat-associated non-ATG (RAN) translational defects. The compounds of the invention were found to inhibit RAN translation but not canonical translation of the downstream open reading frame. We sought to determine if we could design small molecules that address both modes of toxicity using r(CGG)$^{exp}$ as a model system (FIG. 1C). Ideally, the designed compound would improve alternative pre-mRNA splicing defects, inhibit RAN translation, and have no effect on translation of the downstream open reading frame (ORF). It is particularly important that translation of the downstream ORF is not affected; r(CGG)$^{exp}$ is located in the 5' untranslated region (UTR) of the fragile X mental retardation 1 (FMR1) gene, which encode fragile X mental retardation protein (FMRP). FMRP protein is important for regulation of protein synthesis. In fragile X syndrome (FXS), which is also caused by r(CGG) expansion, albeit larger ones than in FXTAS, FMRP is silenced and mice that do not produce FMRP have learning defects and hyperactivity. There are likely spatial aspects that govern whether RAN and/or normal translation is inhibited, as has been previously shown in engineered systems.

r(CUG)$^{exp}$ and Myotonic Dystrophy Type 1 (DM1)

In an effort to develop generalizable methods to design small molecules that affect RNA function, we initiated a program to identify the RNA motifs, or folds, that are privileged for binding small molecules and chemotypes that are privileged for binding RNA. These interactions comprise a database of RNA motif (fold)-small molecule interactions that can inform the design of compounds that bind a target of interest.[5] The database is compared to the secondary structure of an RNA target, and the overlap between them establishes a lead targeting modality. This approach has been validated with various disease-causing RNAs including those that cause myotonic dystrophy types 1 and 2 (DM1 and DM2, respectively).[6] DM1 and DM2 are caused by non-coding, repeating transcripts that fold into hairpins that bind proteins including muscleblind-like 1 protein (MBNL1), a pre-mRNA splicing regulator (FIG. 1A). Sequestration of MBNL1 by the repeating transcripts (RNA gain-of-function) causes its inactivation and hence dysregulation of alternative pre-mRNA splicing.[7]

Previous studies have shown that reactive small molecules target RNA in vivo (*Escherichia coli* and *Saccharomyces cerevisiae* ribosomes)[2a,2b] and in vitro (HIV rev-responsive element (RRE) RNA).[2c] The work described herein utilizes those studies as a launching point for a programmable approach to design small molecules that react with specific transcripts in living cells. That is, information about RNA motif-small molecule interactions informs design of specific small molecules for a target of interest; the small molecules are then coupled with a reactive module that forms a covalent adduct with the transcript in vivo.

We previously designed a compound that improves DM1-associated defects in cellular models of disease using our RNA motif-small molecule database.[6b] The compound, 2H-4, is comprised of a peptoid scaffold that displays two copies of the RNA-binding module Ht (FIG. 1B). Each Ht module binds to one 5'CUG/3'GUC motif displayed in r(CUG)$^{exp}$ [6d] and affords modest potency in vivo.[6b] 2H-4 was engendered with nucleic acid-reactivity by functionalization with chlorambucil (CA),[8] affording 2H-4-CA (FIG. 1B). Thus, the cellular RNAs that react with the nitrogen-mustard type compound CA are dictated by the nature of the RNA-binding modules, which bring the reactive group into close proximity and facilitate adduct formation.

Figure 5:
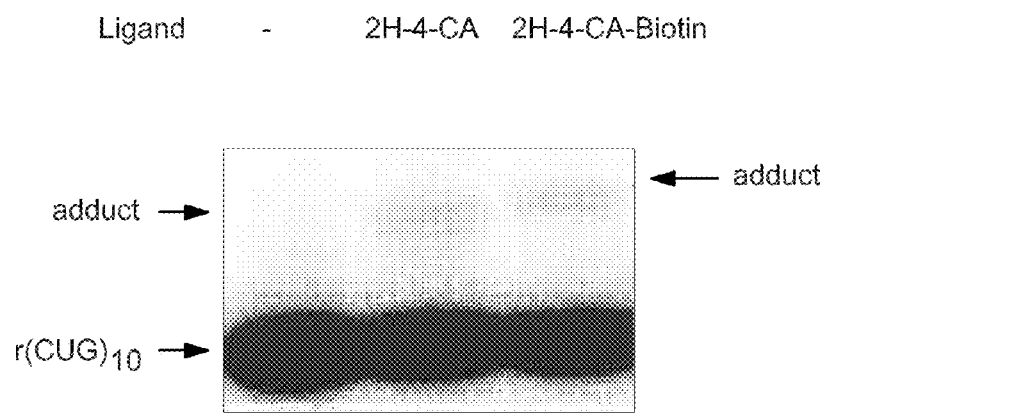
FIG. 5 shows a PAGE gel analysis of the adduct formation of oligonucleotide r(CUG)$_{10}$ (50 nM) with 2H-4-CA and 2H-4-CA-Biotin (10 μM).
Figure 6:
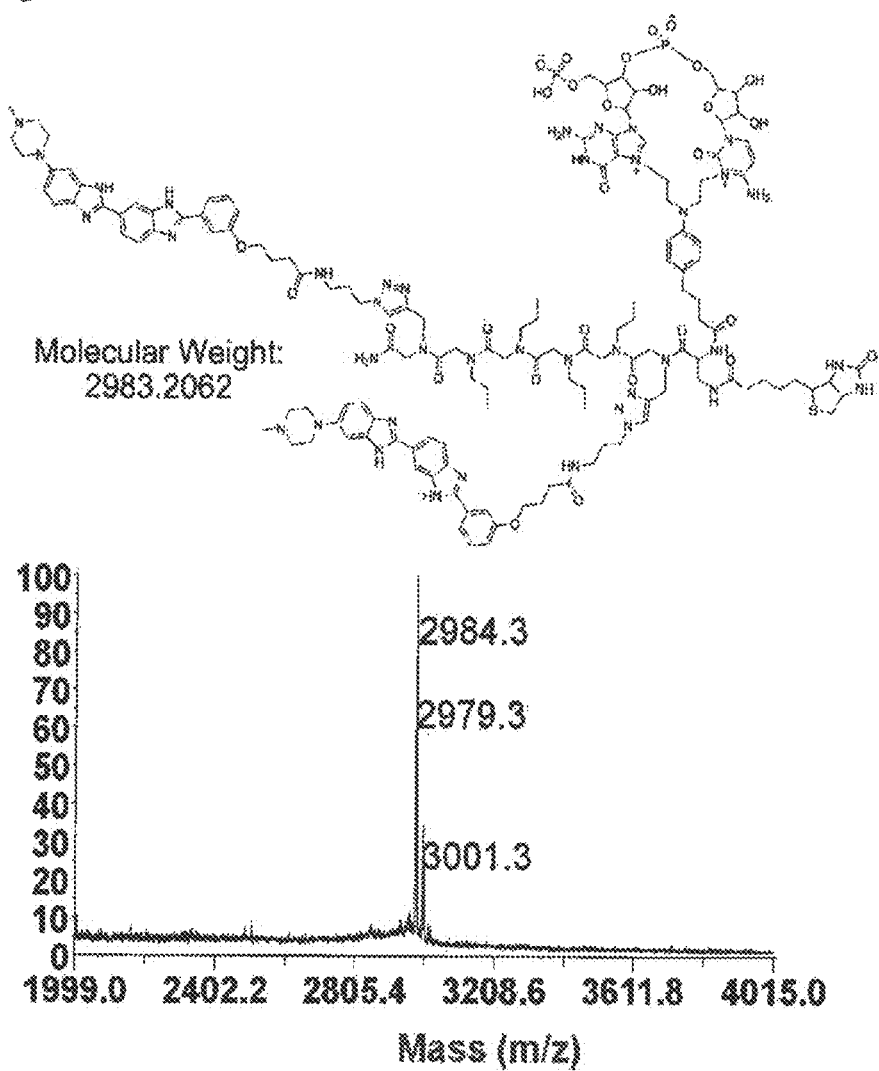
FIG. 6 shows results of a MALDI-TOF MS analysis of r(CUG)$_{10}$-2H-4-CA-Biotin adducts after digestion with P1 nuclease. The observed mass corresponds to an intrastrand cross-linked adduct of a r(GC) dinucleotide with 2H-4-CA-Biotin.
Figure 7:
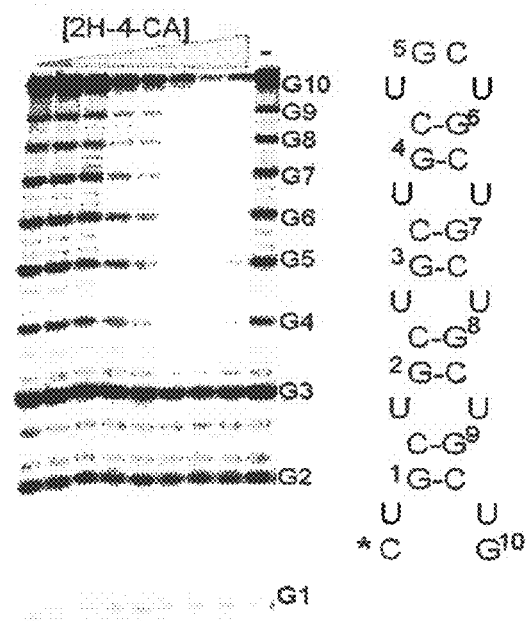
FIG. 7 depicts an electrophoresis gel showing data with respect to RNase T1 digestion of r(CUG)$_{10}$ with various concentration of 2H-4-CA (100, 80, 50, 25, 10, 1, 0.5, 0.1 μM) under denaturing conditions, indicating that adduct formation occurs at G residues. A "–" indicates that no compound was added.
Figure 8:
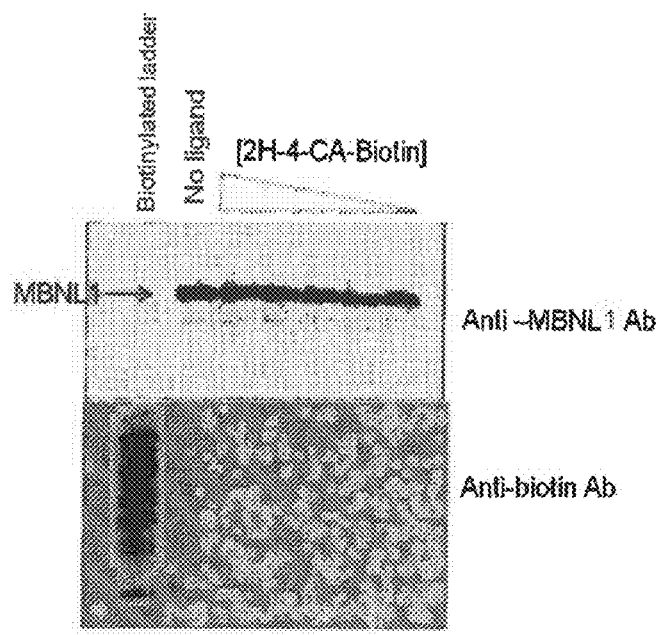
FIG. 8 shows a Western blot of the reaction of MBNL1-His$_6$ with various concentrations of 2H-4-CA-Biotin (100, 50, 10, 1, 0.1 μM) in vitro. Top, western blot probed with an anti-MBNL1 antibody.[2] Bottom, western blot probed with an anti-biotin antibody showing adducts between 2H-4-CA-Biotin and MBNL1 are not formed. (Note that the protein ladder is biotinylated and serves as a positive control for detection of biotin.)

The in vitro potency of 2H-4-CA was compared to the parent compound, 2H-4, using a previously reported assay that measures r(CUG)$_{10}$-MBNL1 complex formation.[6c,9] As summarized in Table 1, 2H-4-CA is ~14-fold more potent than 2H-4. Importantly, 2P-4-CA, which does not contain RNA-binding modules (FIG. 1B), is a weak inhibitor of the r(CUG)$_{10}$-MBNL1 complex as is chlorambucil itself (Table 1). Gel electrophoresis experiments confirm that 2H-4-CA reacts with r(CUG)$_{10}$ in vitro (FIG. 5). The products of the reaction of 2H-4-CA with r(CUG)$_{10}$ were digested with nuclease P1 and analyzed by MALDI MS. Analysis indicates that an intrastrand cross-linked adduct is formed between 2H-4-CA and r(GC) dinucleotides (FIG. 6), likely due to alkylation of guanine N7 and cytosine N3.[10] In addition, RNase T1 digestion of r(CUG)$_{10}$ after incubation with 2H-4-CA confirms that adduct formation occurs at guanosine residues (FIG. 7). Protection from T1 cleavage is observed with as little as 1 μM compound; complete protection is observed with 50 μM 2H-4-CA (FIG. 7). 2H-4-CA was also incubated with MBNL1 and the reaction products analyzed by Western blotting using an anti-MBNL1[11] and anti-biotin antibodies (FIG. 8). These experiments reveal that 2H-4-CA does not react with MBNL1 (FIG. 8), suggesting that the function of MBNL1 is unaffected and potency is solely derived from the reaction of 2H-4-CA with r(CUG)$_{10}$.

TABLE 1

Potency of 2H-4 and derivatives thereof for inhibition of r(CUG)$_{10}$-MBNL1 complex formation.[a]

| Compound | IC$_{50}$ (µM) |
| --- | --- |
| 2H-4 | 71 ± 1 |
| 2H-4-CA | 5 ± 1 |
| 2P-4-CA | 47 ± 2 |
| Chlorambucil | >150 |

[a]Experiments were completed by using a previously described time-resolved FRET assay[9] with minor modifications.

Due to these promising results, 2H-4-CA was evaluated in a model cellular system for improving DM1-associated alternative pre-mRNA splicing defects. In particular, we monitored the improvement of dysregulation of MBNL1 alternative splicing using a previously reported mini-gene (FIG. 2A).[6c] The splicing of MBNL1 pre-mRNA is controlled by MBNL1 itself by binding and repression close to the 3' splice site of exon 5.[12] In the absence of r(CUG)$^{exp}$, MBNL1 exon 5 has an inclusion rate of ~20%; expression of r(CUG)$_{960}$ induces exon inclusion, leading to an inclusion rate of ~40% (FIG. 2A). Thus, compound potency in vivo can be measured by the improvement of MBNL1 splicing dysregulation. Ideally, a compound will completely restore splicing patterns to wild type, i.e., splicing patterns in cells that express r(CUG)$^{exp}$ are indistinguishable from those that do not.

Figure 9:
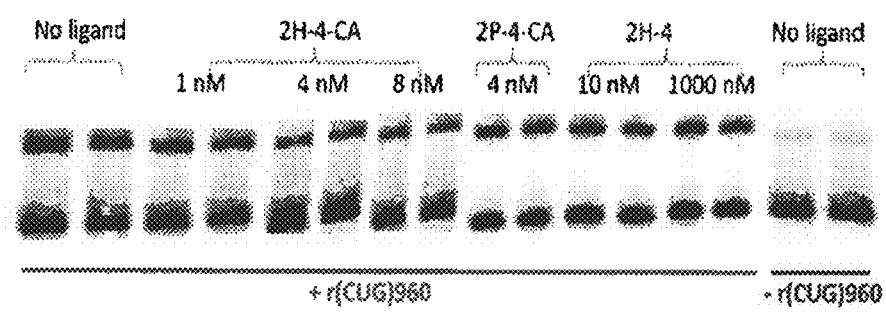
FIG. 9 depicts representative gel images of RT-PCR analysis of alternative pre-mRNA splicing of a MBNL1 bichromatic reporter (RG6)[9] mini-gene in the presence (+r(CUG)960) or absence (−r(CUG)960) of a DM1 mini-gene.[8]
Figure 10:
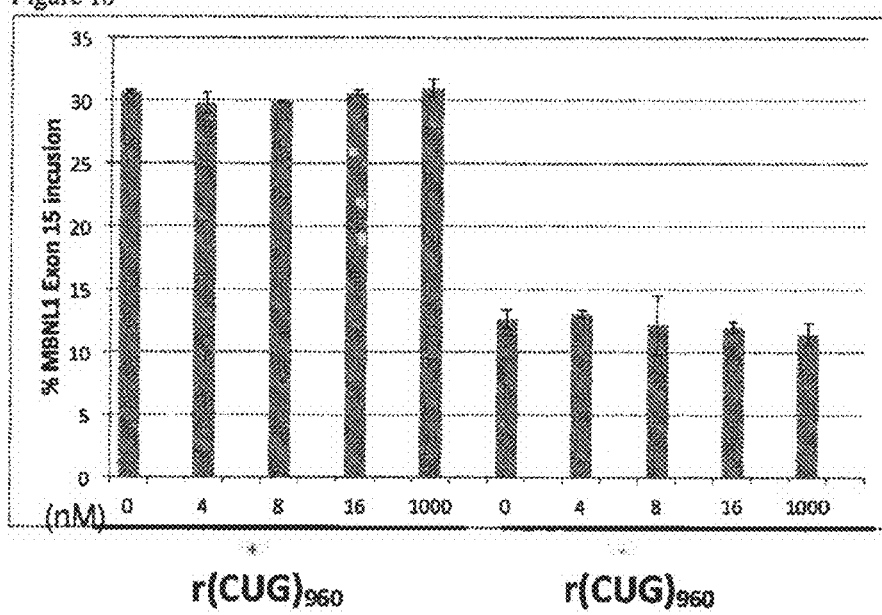
FIG. 10 depicts data in support of the observation that 2H-4-Pt does not improve dysregulation of alternative pre-mRNA splicing. HeLa cells were co-transfected with a DM1 mini-gene that encodes 960 interrupted CTG repeats[8] and a MBNL1 bichromatic reporter (RG6)[9] mini-gene. The percentage of each isoform was determined by RT-PCR and PAGE.

As shown in FIG. 2B, the IC$_{50}$ of 2H-4-CA is 4 nM, where the IC$_{50}$ is the concentration at which splicing patterns are restored to ~30% inclusion of exon 5 (FIGS. 2B and 9). 2H-4-CA's effect plateaus at doses up to 4 nM and then diminishes at higher concentrations, perhaps reflecting non-specific interactions. (Note: 2P-4-CA shows some activity at 16 nM (FIG. 2B)). Since this compound lacks the RNA-binding modules, it likely also interacts with other biomolecules that could give rise to non-specific effects.) Neither the control compound 2P-4-CA nor 2H-4 has any effect on alternative pre-mRNA splicing at these concentrations (FIGS. 2B and 9).[13] In fact, 2H-4-CA is the most potent compound known to date that improves DM1-associated pre-mRNA splicing defects.[14]

Figure 11:
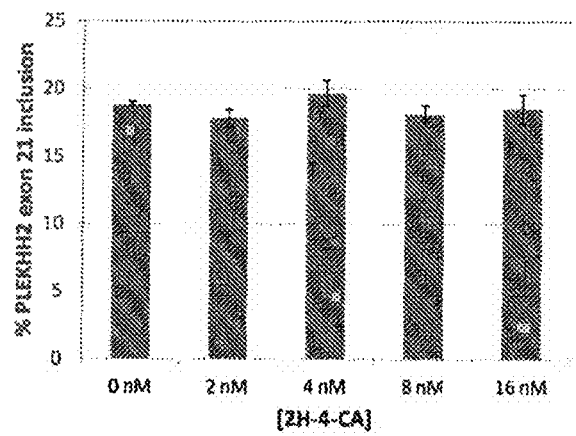
FIG. 11 depicts data in support of the observation that 2H-4-CA does not affect the alternative splicing of PLE-KHH2, which is not controlled by MBNL1. HeLa cells were co-transfected with a DM1 mini-gene that encodes 960 interrupted CTG repeats and a mini-gene that reports on the alternative splicing of PLEKHH2.[8] The percentage of each isoform was determined by RT-PCR and PAGE.

Moreover, it is ~2500-fold more potent than the parent compound, 2H-4, which has an IC$_{50}$ of ~10 µM (FIG. 2B). Importantly, 2H-4-CA does not affect the alternative splicing of a transcript that is not regulated by MBNL1, illustrating selectivity for targeting r(CUG)$_{960}$ (FIG. 11). In summary, our investigations show that 2H-4-CA improves pre-mRNA splicing defects caused by r(CUG)$^{exp}$ and that compound potency in vivo is drastically improved by covalent adduct formation.

There is a significant difference in 2H-4-CA's in vitro IC$_{50}$ for inhibiting r(CUG)$_{10}$-MBNL1 complex formation and its in vivo IC$_{50}$ for improving splicing defects (Table 1 and FIG. 2B). These observations could be due to: (i) differences in repeat length in vitro (r(CUG)$_{10}$) and in vivo (r(CUG)$_{960}$); (ii) differences in incubation time and temperature (4 h/room temperature in vitro vs. 20-24 h/37° C. in vivo). In vitro potency is improved by ~2.5-fold by increasing the incubation time and temperature; or (iii) the two assays measure very different phenomena: in vitro assays measure inhibition of complex formation (all or none) while in vivo assays measure MBNL1 activity (degree of restoration). A recent report showed that the amount of active MBNL1 has a graded effect on the severity of splicing dysregulation.[15] That is, only partial inhibition of the r(CUG)$^{exp}$-MBNL1 can cause significant improvement of splicing defects.

Figure 12:
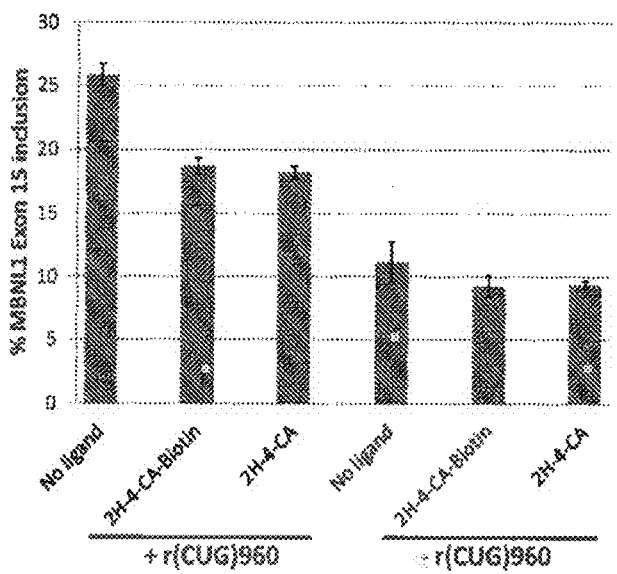
FIG. 12 shows data with respect to the biotinylation of 2H-4-CA (2H-4-CA-Biotin) (4 nM) does not affect its bioactivity as determined by improvement of MBNL1 alternative splicing, which is regulated by MBNL1.[9] HeLa cells were co-transfected with a DM1 mini-gene that encodes 960 interrupted CTG repeats[8] and a reporter that contains human muscleblind exon 5 and adjacent introns (FIG. 2A).[9] The percentage of each isoform was determined by RT-PCR and PAGE.

The cellular targets of 2H-4-CA were identified using a biotinylated derivative, 2H-4-CA-Biotin (FIG. 3A). (There is no difference in the in vivo potencies of 2H-4-CA-Biotin and 2H-4-CA (FIG. 12).) In these studies, cells were treated with 4 nM 2H-4-CA-Biotin, allowing formation of 2H-4-CA-Biotin-biomolecule adducts in vivo. Adducts were isolated from the cells using TRIzol reagent and streptavidin beads. The beads were washed exhaustively with 1×PBST then water. 2H-4-CA-Biotin adducts were eluted by heating the beads at 65° C. in 95% formamide. Gel electrophoresis and northern blotting of the eluted fraction showed that 2H-4-CA-Biotin reacts with r(CUG)$_{960}$ (FIG. 3B). Next, these pull-down experiments were completed with 4 nM 2H-4-CA and varying concentrations of 28-4; 2H-4 should compete with 2H-4-CA for binding, reducing adduct formation between targets that are specifically bound by 2H-4. Indeed, 2H-4 inhibits adduct formation between 2H-4-CA and r(CUG)$^{exp}$ at micromolar concentrations (FIGS. 3B and C), demonstrating that both compounds recognize r(CUG)$_{960}$ in vivo.

Figure 13:
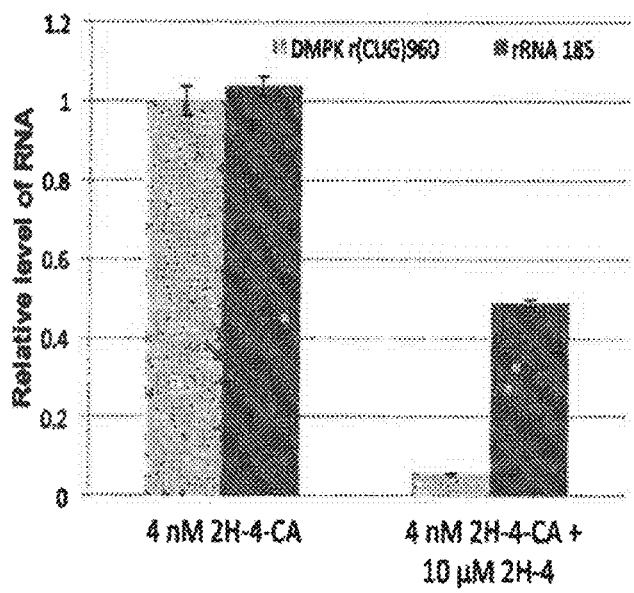
FIG. 13 shows results of qRT-PCR analysis of 18S rRNA and r(CUG)$^{exp}$ isolated from cells treated with 2H-4-CA in the presence and absence of 2H-4. 2H-4 competes with 2H-4-CA for binding to cellular targets. These studies show that 2H-4 binds more specifically to r(CUG)$^{exp}$ (~20-fold reduction) than 18S rRNA (~2-fold reduction).

These results were further investigated by using qRT-PCR (FIG. 13). The amounts of 18S rRNA and r(CUG)$^{exp}$ pulled down from cells treated with 4 nM 2H-4-CA is similar. However, when cells are treated with 4 nM 2H-4-CA and 10 µM 2H-4, the amount of r(CUG)$^{exp}$ is reduced by ~20-fold while the amount of 18S rRNA is only reduced by ~2-fold. Such competition experiments can be used to control for targets non-selectively pulled down by reaction with alkylators. Importantly, western blotting shows 2H-4-CA-Biotin does not react with MBNL1 (FIG. 3D, left; probed with anti-MBNL1)[11] or other proteins (FIG. 3D, right; probed with anti-biotin) in cellular pull-down experiments.

Figure 14:
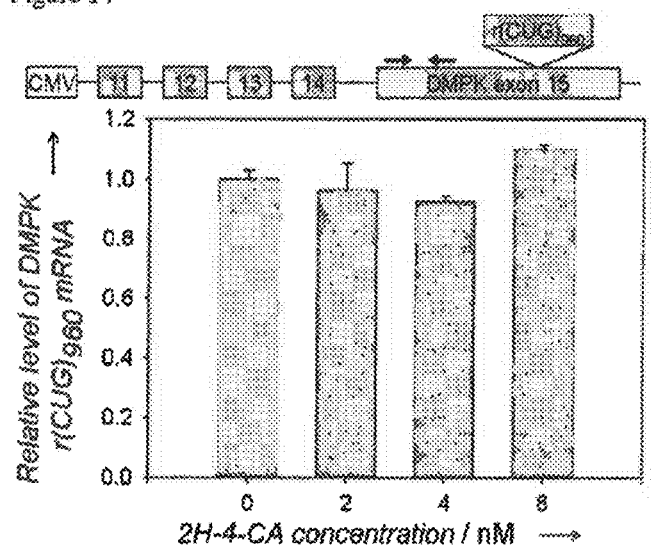
FIG. 14 shows results of real-time RT-PCR analysis of r(CUG)$_{960}$-containing mRNA expression after treatment with 2H-4-CA. Top, schematic of the DMPK mRNA mini-gene in which r(CUG)$_{960}$ is expressed. Arrows indicate primer positions. Bottom, real time RT-PCR data showing that adduct formation does not induce degradation of alkylated r(CUG)$_{960}$. These studies prove that improvement of pre-mRNA splicing defects is due to covalent adduct formation between 2H-4-CA and r(CUG)$_{960}$ and not reaction-stimulated mRNA degradation.

To investigate the source of the improved potency of 2H-4-CA, we studied whether adduct formation induces degradation of r(CUG)$^{exp}$ as its degradation would also lead to improvement of DM1-associated defects.[16] Real-time RT-PCR experiments of cellular RNA harvested after reaction with 2H-4-CA show that r(CUG)$^{exp}$-mRNAs containing covalent adducts are not degraded more than those that do not (FIG. 14). These studies suggest that covalent adduct formation alone is responsible for the ~2500-fold enhancement in the activity of 2H-4-CA, not reaction-induced mRNA degradation.

In summary, we have demonstrated that the potency of designer small molecules that solely bind RNA targets can be improved by engendering them with the ability to react with their cellular targets. Moreover, adduct formation provides a potentially general method to identify the cellular targets of RNA-directed small molecules in living cells and, perhaps, animal models of disease. Such transcriptome-wide probing could identify bystander (unintended) targets, and such information could be used to design and identify compounds with improved selectivity akin to activity-based profiling approaches used for proteins.[17]

r(CGG)exp and Fragile X-associated Tremor/Ataxia Syndrome (FXTAS)

Previously, we designed the small molecule 2H-5 (FIG. 15) to target r(CGG)$^{exp}$ by mining interactions in a RNA-motif small molecule database. The compound contains two RNA-binding modules (H) that are appropriately spaced to target two 5'CGG/3'GGC motifs in r(CGG)$^{exp}$ simultaneously.[18] Indeed, 2H-5 improves pre-mRNA splicing defects caused by sequestration of Sam68 at µM concentrations and does not affect translation of a model downstream ORF.[18] In this study, we sought to improve the potency of 2H-5 by appending it to a reactive module akin to our previously reported studies of a designed small molecule that targets r(CUG)$^{exp}$, the causative agent of myotonic dystrophy type 1. To engender 2H-5 with the ability to react with cellular RNA targets, it was coupled to a nitrogen-mustard compound (chlorambucil; CA). Since chlorambucil preferentially reacts with the N-7 of G, we hypothesized that the r(CGG) repeats in FXTAS might be an ideal RNA to which to extend our approach. A biotin tag was also incorporated to allow for the facile isolation of the RNA targets it binds in cellulo, affording 2H-5-CA-Biotin. We also synthesized a control compound that lacks the RNA-binding modules, or 2P-5-CA-Biotin.

Figure 16:
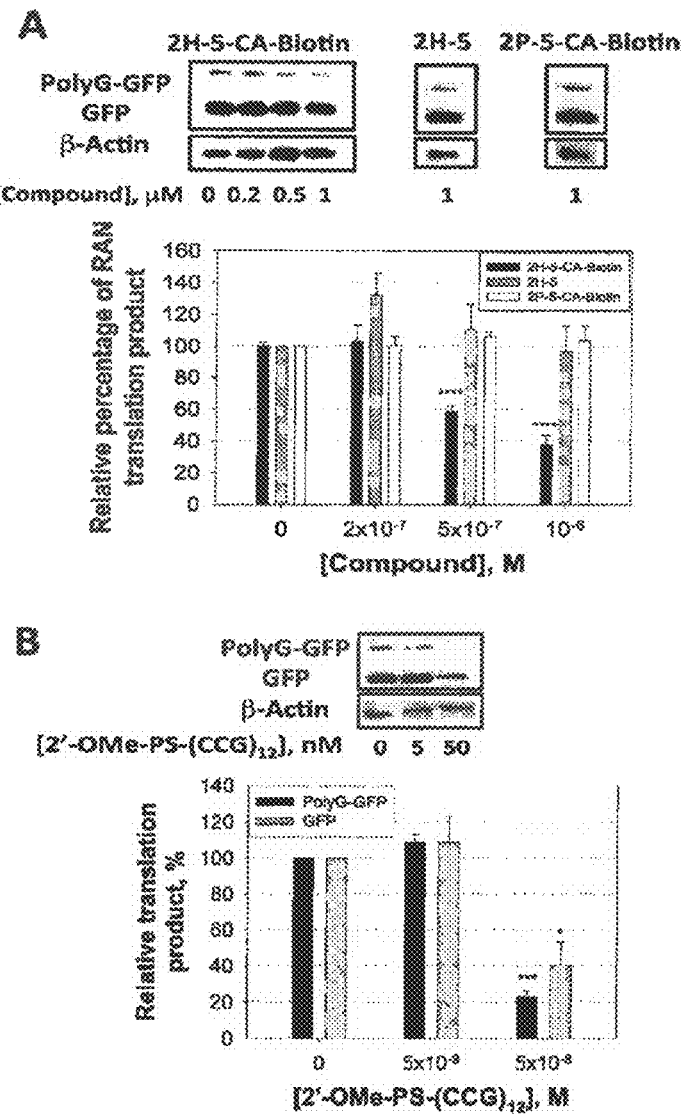
FIG. 16 shows an analysis of the cellular targets of small molecules (A) and the effects of small molecules and oligonucleotide on protein translation in cellulo via Western blot (B, C). A, results of qRT-PCR of the starting lysate and the pulled-down fraction of cells treated with 500 nM 2H-5-CA-Biotin and 2P-5-CA-Biotin. These studies show that a major cellular target of the designer small molecule is r(COG)$_{88}$. B, effect of 2H-5, 2P-5-CA-Biotin, and 2H-5-CA-Biotin on RAN translation of r(CGG)$^{exp}$ and normal translation of the downstream ORF, which encodes GFP. C, effect of a 2'OMe phosphorothioate oligonucleotide, 2'OMe-PS-(CCG)$_{12}$, on RAN and canonical translation. "*", "", "*" and "****" denote p<0.05, p<0.01, p<0.001 and p<0.0001, respectively, as determined by a two-tailed Student t-test.

Compounds were first evaluated for recognizing their RNA targets in cellulo by using a reactive profiling approach termed Chem. CLiP (CHEMical Cross-Linking and Pull down, or a small molecule approach that is similar to cross-linking and immunopreciptation (CLIP)).[3] Cells expressing r(CGG)$^{exp}$ were treated with 500 nM 2H-5-CA-Biotin or the control compound that does not contain RNA binding modules, 2P-5-CA-Biotin, and cellular targets were isolated using streptavidin beads. Bound targets were released from the resin and analyzed for RNA content via qRT-PCR (FIG. 15). Relative to the starting lysate, there was an 24-fold enrichment of r(CGG)$_{88}$-GFP in the fraction of pulled down when 2H-5-CA-Biotin is used. When the control compound 2P-5-CA-Biotin is used, there is 50% less r(CGG)$_{88}$-GFP in the pulled down fraction. At the same experiment with cells expressing GFP mRNA, only 2-fold more GFP mRNA was pulled down in the absence of r(CGG)$^{exp}$ by 2H-5-CA-Biotin (FIG. 16A). These studies show that 2H-5-CA-Biotin binds and reacts with the intended target in cellulo.

Figure 17:
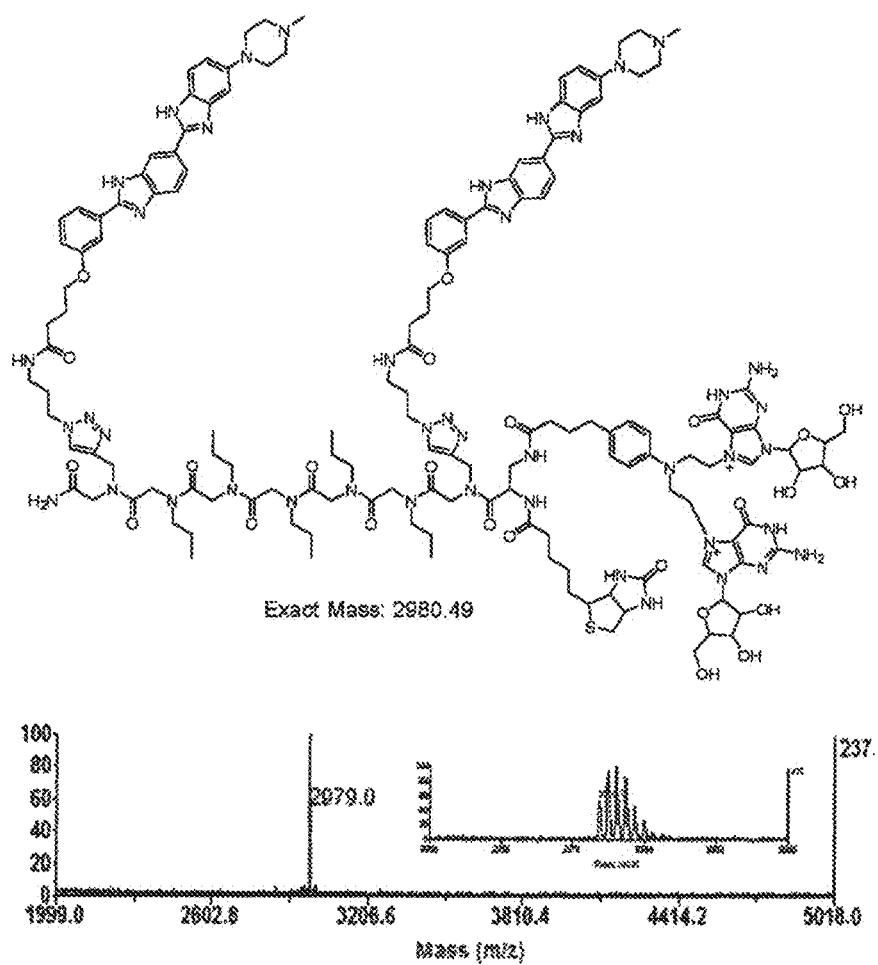
FIG. 17 MALDI-TOF MS analysis of r(CGG)$_{60}$-2H-5-CA-Biotin adducts after digestion with P1 nuclease. The observed mass corresponds to the adduct of 2H-5-CA-Biotin with two guanosines.

The products of the reaction between 2H-5-CA-Biotin and r(CGG)$^{exp}$ were further studied. The compound 2H-5-CA-Biotin was incubated in vitro with r(COG)$_{60}$. Purification of the products of reaction and cleavage by P1 nuclease were completed to isolate the 2H-5-CA-Biotin-RNA products that were identified by mass spectral analysis. The observed mass of the reaction products corresponds to a 2H-5-CA-Biotin adduct that reacted with two guanosines (FIG. 17), which is consistent with the preferred reactivity of chlorambucil, the N-7 of guanine.

Thus, both of these studies show that 2H-5-CA-Biotin reacts with r(CGG)$^{exp}$ and thus we sought to study the biological consequences of this reaction. For example, we studies the effect on improvement of pre-mRNA splicing defects in FXTAS model systems and the ability to affect translation of r(CGG) repeats without a canonical translation start (ATG) site when the r(CGG) repeat is placed in the 5'UTR in a GFP mRNA construct.

Figure 18:
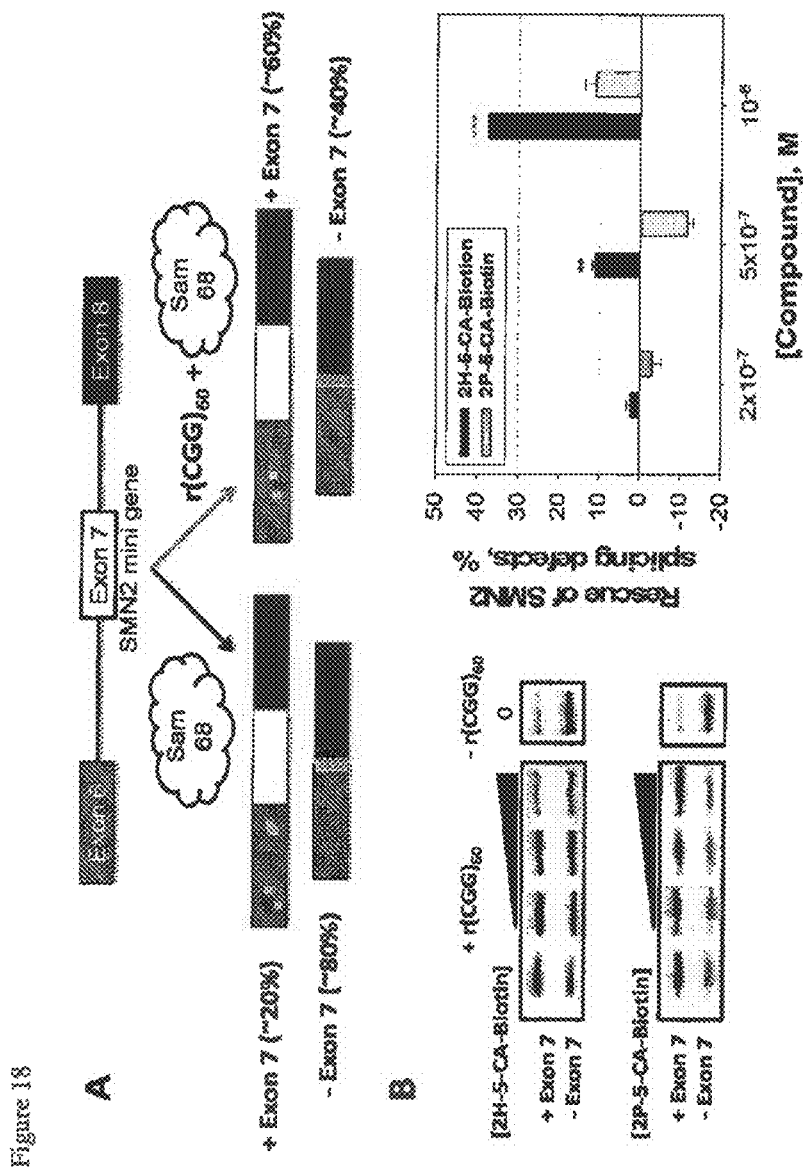
FIG. 18. A. Schematic of the alternative pre-mRNA splicing of SMN2 mini-gene. B. In cellulo efficacy of 2H-5-CA-Biotin and 2P-5-CA-Biotin against FXTAS as assessed by improvement in SMN2 pre-mRNA splicing defects. "" and "*" denote p<0.01 and p<0.001, respectively.

The ability of 2H-5-CA-Biotin to improve FXTAS-associated pre-mRNA splicing defects was tested in cellulo using a plasmid that encodes r(CGG)$_{60}$ and a mini-gene to study the alternative splicing of survival motor neuron 2 (SMN2) mRNA. It was previously shown that the alternative splicing of SMN2 exon 7 is dysregulated by sequestration of Sam68 by r(CGG)$^{exp}$.[8] In the presence of r(CGG)$_{60}$, ≈60% of exon 7 is included in the mature mRNA while in the absence of r(CGG)$_{60}$, ≈20% of exon 7 is included (FIG. 18A). Treatment of cells with 1 μM of 2H-5-CA-Biotin, improved the SMN2 splicing defect by 40% (FIG. 18B).

Figure 19:
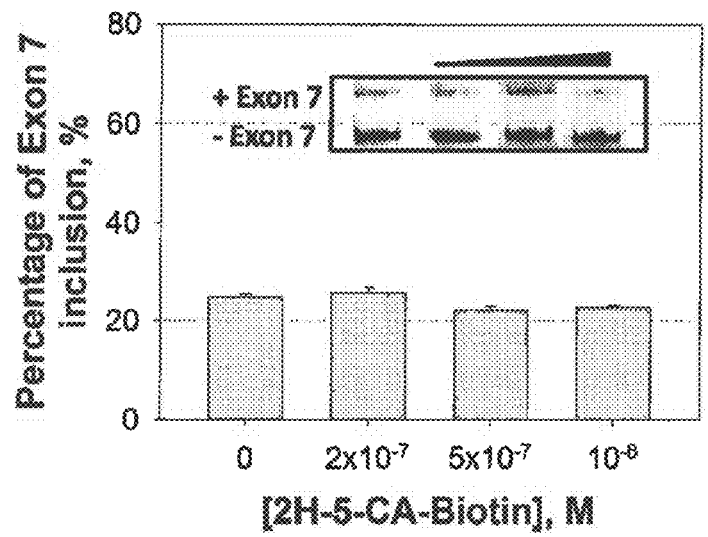
FIG. 19. Plot of percentage of SMN2 exon 7 inclusion in the absence of r(CGG)$_{60}$ and gel images. No statically significant effect on SMN2 pre-mRNA splicing in the absence of r(CGG)$_{60}$ was observed, suggesting that the improvement of pre-mRNA splicing defects is due to 2H-5-CA-Biotin displacing proteins from r(CGG)$_{60}$.
Figure 20:
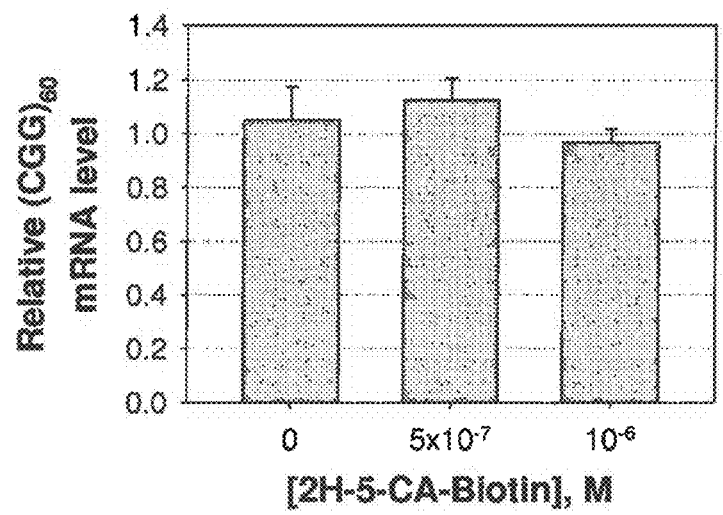
FIG. 20. Real-time RT-PCR analysis of (COG)$_{60}$ mRNA expression after treatment with 2H-5-CA-Biotin. The amount of mRNA was normalized relative to β-actin.

No effect was observed on SMN2 splicing in cells that did not express r(CGG)$_{60}$ (FIG. 19). Further, no significant effect on SMN2 splicing was observed when cells were treated with 1 μM 2H-5 or 2P-5-CA-Biotin, showing that covalent binding and the RNA-binding modules are required for the observed bioactivity of 2H-5-CA-Biotin (FIG. 18B). The observed bioactivity is not due to changes in r(CGG)$^{exp}$ abundance as determined by qRT-PCR (FIG. 20). Taken together, these data indicate that 2H-5-CA-Biotin's mode of action is displacement of proteins from r(CGG)$_{60}$.

Figure 21:
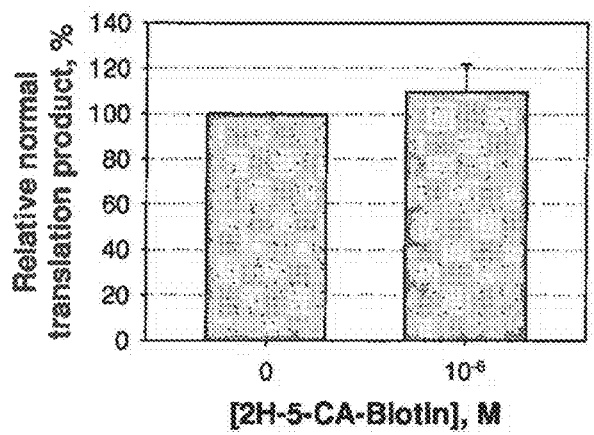
FIG. 21. Plot of relative normal translation product expression after 2H-5-CA-Biotin treatment of COS7 cells transfected with a plasmid encoding (CGG)$_{88}$-GFP. The amounts of GFP were normalized to β-actin and no significant change was observed.

Next, we studied if 2H-5-CA-Biotin inhibits translation events of a r(CGG)$^{exp}$-containing transcript, namely both RAN and canonical translation. For these studies, we employed a cellular model system in which r(CGG)$_{88}$ is embedded in the 5' UTR of green fluorescent protein (GFP). The construct was developed such that the orientation of the r(CGG) in the 5' UTR relative to the GFP open reading frame mimics that between r(CGG)$^{exp}$ and the ORF in FMR1. Two translation products are observed in cellulo, the normal translation product GFP and the RAN translation product polyG-GFP. The two products can be resolved by SDS-PAGE and visualized by Western blot with an anti-GFP antibody. Indeed, 2H-5-CA-Biotin decreases the formation of the RAN translation product with an IC$_{50}$ of ~500 nM (FIG. 16B) but does not affect translation of GFP at the canonical translational start site (FIG. 21).

Figure 22:
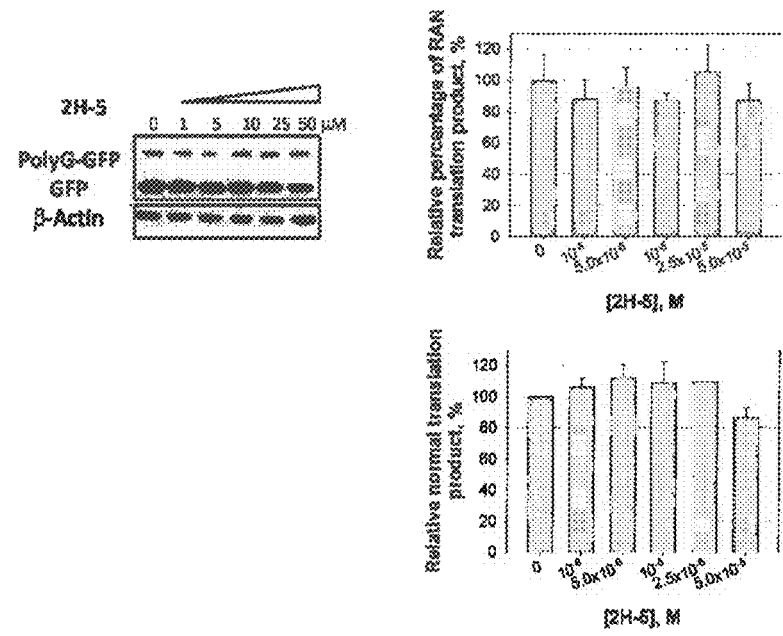
FIG. 22. Western blot images and plots of relative percentage of RAN translation product and normal translation product (normalized to r2H-5 treatment of COS7 cells transfected with a plasmid encoding (CGG)$_{88}$-GFP. The amounts of GFP were normalized to β-actin.
Figure 23:
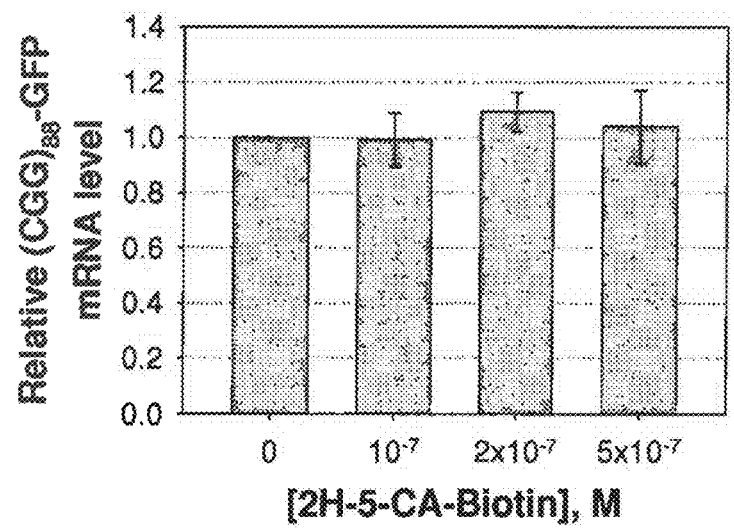
FIG. 23. Real-time RT-PCR analysis of r(CGG)$_{88}$-GFP mRNA expression after treatment with varying concentrations of 2H-5-CA-Biotin. The amount of mRNA was normalized relative to β-actin.
Figure 24:
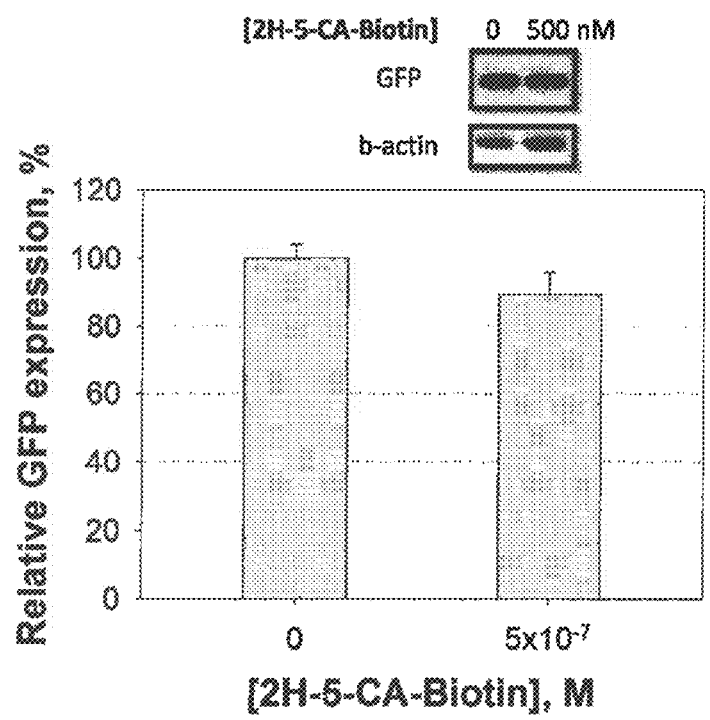
FIG. 24. Western blot images and plots of relative GFP expression (normalized to β-actin. blot images 2H-5-CA-Biotin treatment of COS7 cells with a GFP construct that lacks r(CGG)$_{88}$ in the 5' UTR.

Compounds 2H-5 (evaluated up to 50 μM) and 2P-5-CA-Biotin (evaluated up to 1 μM) do not affect either translational event at any concentration tested (FIGS. 16B and 22). As observed in our splicing studies, 2H-5-CA-Biotin does not affect (CGG)$_{88}$-GFP mRNA levels or translation of GFP when the 5' UTR lacks r(CGG)$^{exp}$ (FIGS. 23 and 24). Thus, it is possible to inhibit RAN translation of an expanded repeat embedded in a 5' UTR with a small molecule without affecting the downstream ORF.

Figure 25:
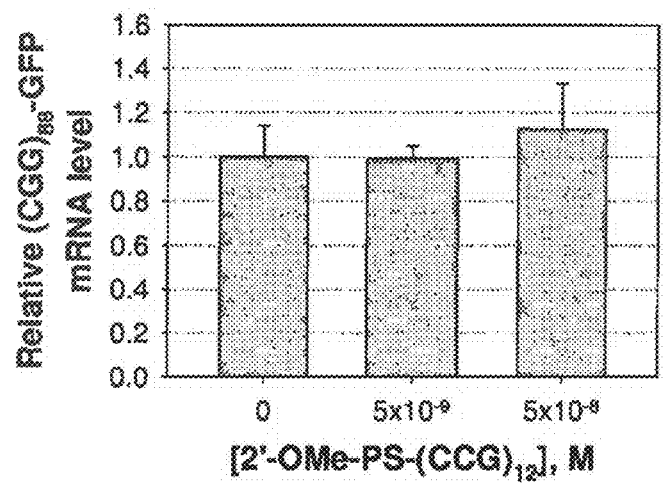
FIG. 25. Real-time RT-PCR analysis of r(CGG)$_{88}$-GFP mRNA levels after treatment with varying concentrations of oligonucleotide, 2'-OMe-PS-(CCG)$_{12}$. The amount of mRNA was normalized relative to β-actin.
Figure 26:
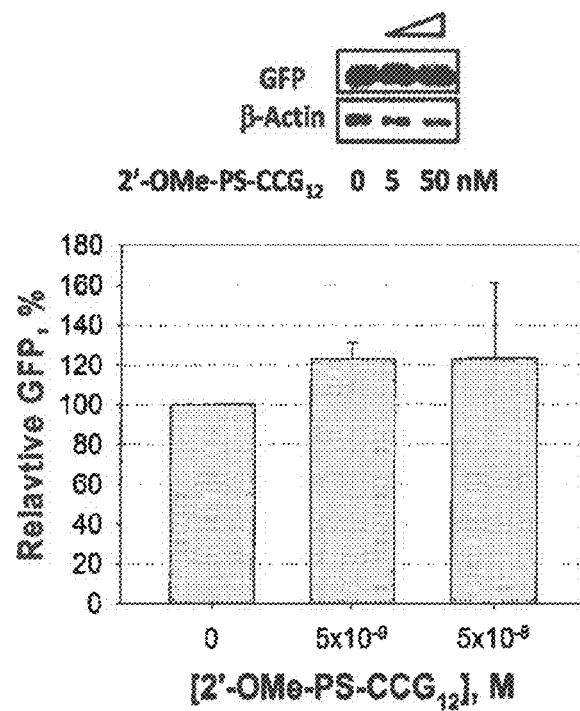
FIG. 26. Western blot images and plots of relative GFP expression (normalized to β-actin. expression) 2'-OMe-PS-CCG12 treatment of COS7 cells with a GFP construct that lacks r(CGG)$_{88}$ in the 5' UTR.

We also studied if a 2'OMe phosphorothioate oligonucleotide complementary to r(CGG)$^{exp}$ can selectively inhibit RAN translation events. As shown in FIG. 16C, the oligonucleotide inhibits both RAN and normal translation; no change in (CGG)$_{88}$-GFP mRNA levels was observed when cell were treated with oligonucleotide (FIG. 25). The oligonucleotide has no effect on translation of GFP if the 5' UTR lacks r(CGG)$^{exp}$ (FIG. 26).

We have demonstrated that designer small molecules binding RNA targets covalently more potently improve pre-mRNA splicing defects than the unreactive parent compound and selectively inhibit the toxic RAN translation product in a model FXTAS cellular system. Our studies are one of the first demonstrations that a small molecule can inhibit a RAN translational product and opens up pathways to develop chemical probes to study this aspect of disease pathology. Compounds that modulate non-canonical translational events could have broad applicability. For example, proteome-wide profiling in viruses and human cell lines have shown that many peptides are translated without the use of start codons.

Compositions and Methods of the Invention

Accordingly, in various embodiments, the invention provides a compound of formula (I)

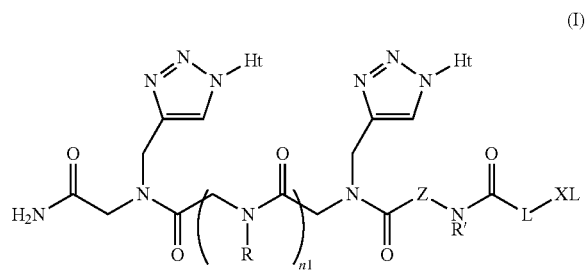

wherein each individually selected R or R' is H or (C1-C6)alkyl;

n1 is 2, 3, 4, 5, or 6;

Z is a (C1-C3)alkylene group, optionally substituted with a reporter or affinity group;

L is a linker group comprising an optionally substituted (C1-C6)alkylene, wherein one or two carbon atoms is optionally replaced by O;

XL is an RNA-reactive crosslinking group;

each individually selected Ht is a group of formula

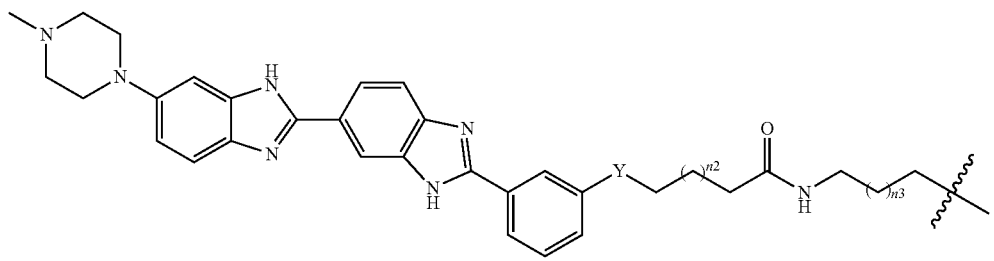

wherein
n2 is 0, 1, 2, or 3;
n3 is 0, 1, 2, or 3;
Y is O or CH$_2$;
a wavy line indicates a point of bonding;
or any tautomer thereof; or any salt thereof, or any stereoisomer thereof.

By a tautomer thereof is meant a compound related to the structure as shown only be relocation of a hydrogen atom. Within the present invention it is to be understood that a compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, for the group Ht, a formula can be shown as follows:

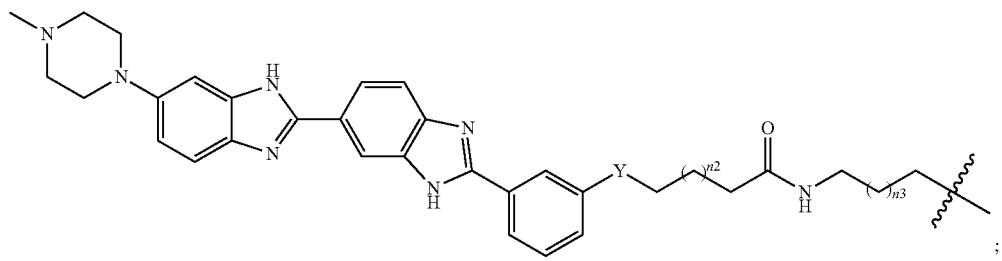

however, this formula is intended to encompass all tautomeric forms, including tautomeric forms of the benzimidazole groups. These include formulas such as:

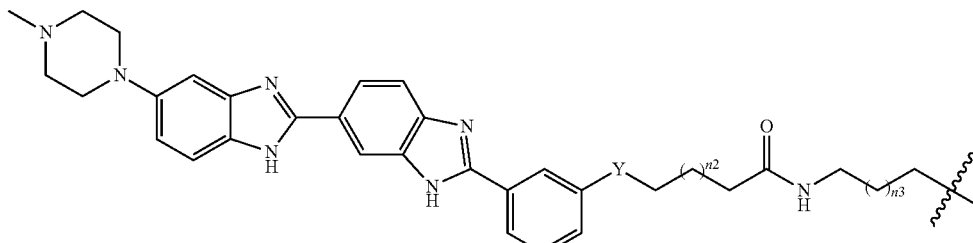

,

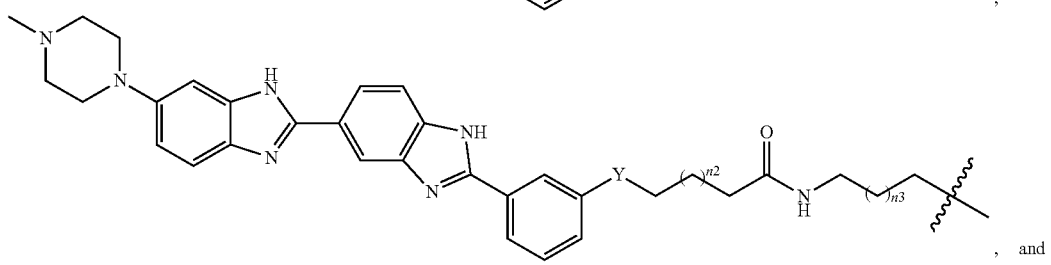

, and

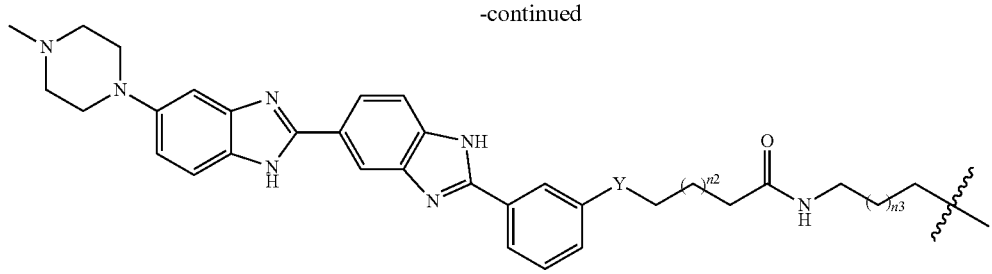

which are all isomeric forms due to benzimidazole tautomerism, thus are tautomers and are included in the specification of the formulas herein and are understood to be disclosed and claimed herein.

By a "stereoisomer" thereof is meant any enantiomer or diastereomer of a molecular falling within the definition of formula (I) in any of its embodiments is included in the compositions of matter disclosed and claimed herein.

More specifically, the invention can provides a compound of formula (I) wherein the compound is

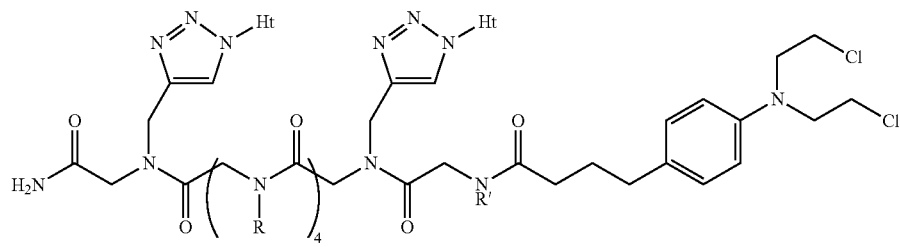

or the compound is

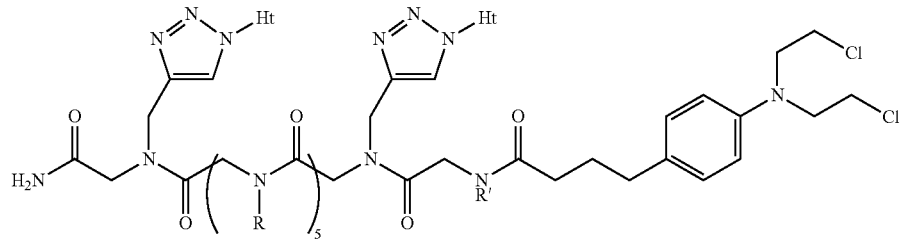

wherein Ht, R, and R', are as defined herein;
or any tautomer thereof; or any salt thereof, or any stereoisomer thereof.

In various embodiments, the group Ht can be

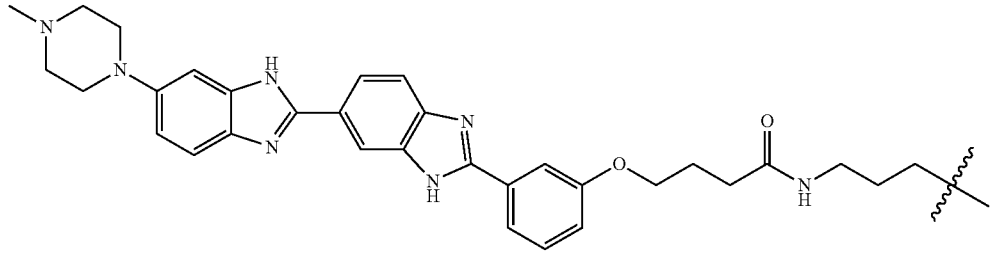 [SMILES: *CCCNC(=O)CCCOc1cccc(-c2nc3ccc(-c4nc5ccc(N6CCN(C)CC6)cc5[nH]4)cc3[nH]2)c1]

wherein a wavy line indicates a point of bonding;
R is n-propyl; R' is H; or any combination thereof;
or any tautomer thereof; or any salt thereof, or any stereoisomer thereof.

For example, the compound can be 2H-4-CA, of formula

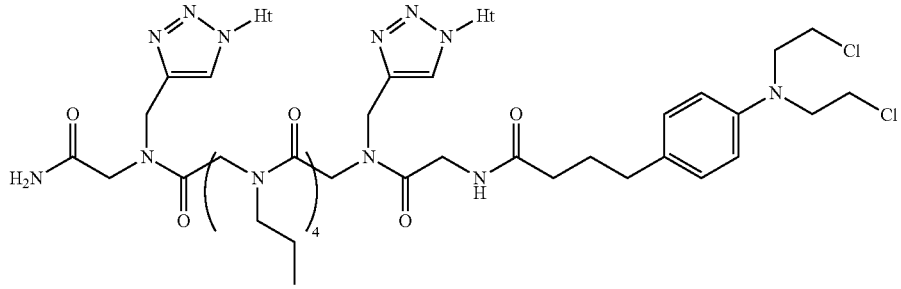

or can be compound 2H-5-CA, of formula

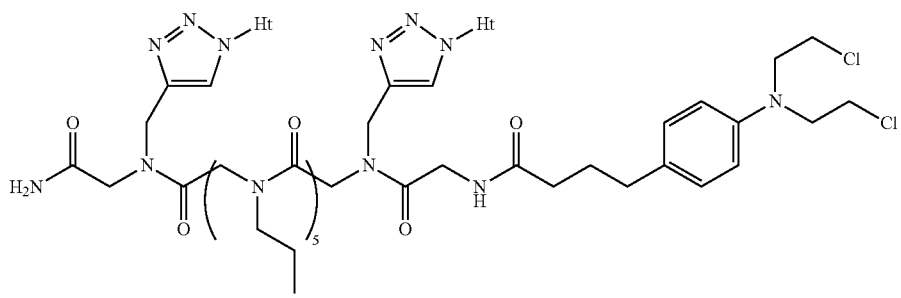

wherein Ht is a group of formula

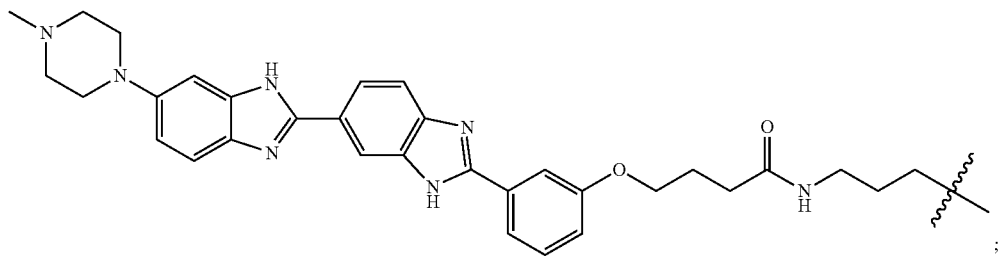 [SMILES: *CCCNC(=O)CCCOc1cccc(-c2nc3ccc(-c4nc5ccc(N6CCN(C)CC6)cc5[nH]4)cc3[nH]2)c1]

wherein a wavy line indicates a point of bonding;
or any tautomer thereof; or any salt thereof, or any stereoisomer thereof.

In some embodiments, Z is an unsubstituted alkylene group. In other embodiments, the group Z can provide a point of attachment of a reporter or an affinity group to the sequence-specific RNA-binding molecule of formula (I), such as wherein Z is an alkylene group substituted with a biotin-comprising moiety. The reporter group can be bonded to the Z alkylene group by an alkylene chain, optionally comprising one or more carboxamido or carboxyester groups therein. The terms a "reporter" group, or an "affinity" group as the terms are used herein refer to groups that either have a reporter function enabling visualization of bonding, localization, etc. of the molecule, e.g., by fluorescence, radioactivity, or the like, or have an affinity function that enables their detection or binding by a complementary affinity group, e.g., biotin-avidin affinity. For example, the compound of formula (I) comprising a reporter or affinity group can be of formula

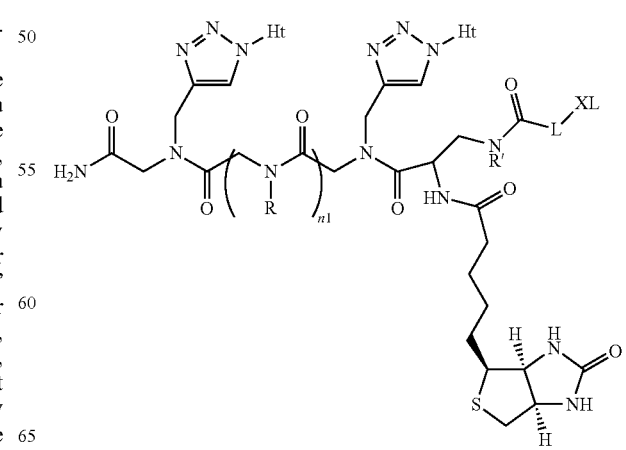

wherein Ht, R, R', n1, L, and XL, are as defined herein.

More specifically, the compound can be 2H-4-CA-biotin of formula

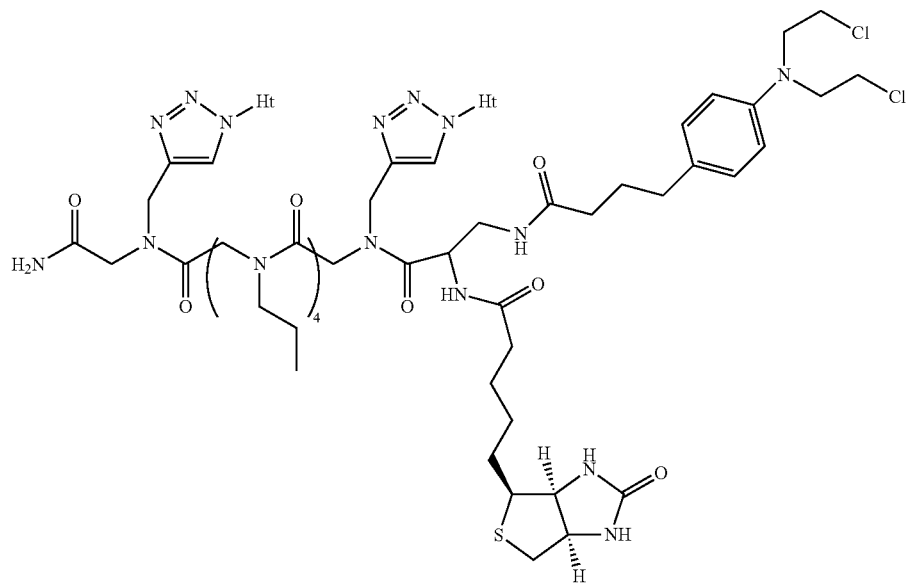

or can be compound 2H-5-CA-biotin of formula

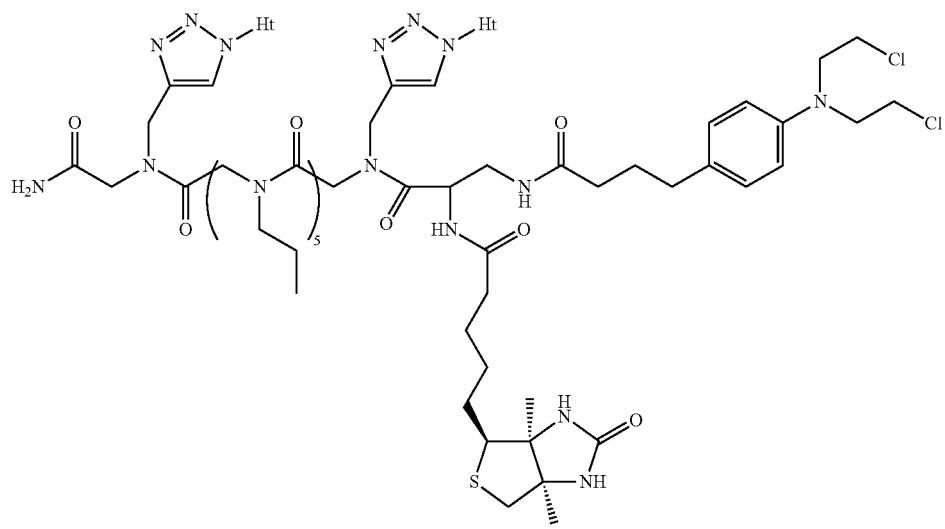

or any tautomer thereof; or any salt thereof, or any stereoisomer thereof.

The compounds of the invention as disclosed and claimed herein can, as described above, form a covalent complex with RNA. Accordingly, in various embodiments the invention provides a covalently-linked complex of the compound of formula (I) and a segment of RNA comprising a hairpin loop. The RNA can comprise an $r(CUG)^{exp}$ segment. By this covalent interaction, the binding of the complex comprising the $r(CUG)^{exp}$ segment with muscleblind-like 1 protein (MBL1) is reduced compared to the binding of a comparable RNA sequence not covalently linked to the compound of formula (I). Or the RNA can comprise an $r(CGG)^{exp}$ segment. By this covalent interaction, the binding of the complex comprising the $r(CGG)^{exp}$ segment with DiGeorge Syndrome Critical Region 8 protein (DGCR8), or Src-associated in mitosis, 68 kDa protein (Sam68), is reduced compared to the binding of a comparable RNA sequence not covalently linked to the compound of formula (I).

In some embodiments, the crosslinking group can comprise an alkylating group, e.g., the (β-chloroethyl)amino group, a "nitrogen-mustard" group, of chlorambucil. In other embodiments, the crosslinking group can comprise a triggered cross linker using photochemical or shape-triggered catalysis, e.g., use of the reactive fragment of duocarmycin, as described in: "Asymmetric synthesis of 1,2,9,9a-tetrahydrocyclopropa[c]benzo[e]indol-4-one (CBI)", J P Lajiness and D L Boger (2011), *J. Org. Chem.*, 76(2), 583-7; see also "Transcriptome-wide identification of RNA-binding protein and microRNA target sites by PAR-CLIP", M Hafner et al. (2010), *Cell,* 141(1), 129-141; both of which publications are incorporated by reference herein in their entireties.

Formation of the covalently-linked complex of the compound of formula (I) with RNA provides, in various embodiments, a method of inactivating an RNA, comprising contacting the RNA with a compound of the invention, wherein inactivating the RNA comprises interfering with molecular associations that the RNA makes in a living cell, wherein the RNA and the compound form a covalent bond to provide a covalently-linked complex. The RNA sequence or segment that reacts with the compound of formula (I), as discussed above, can comprises a hairpin loop, and can comprise an $r(CUG)^{exp}$ segment or a an $r(CgG)^{exp}$ segment. For example, interfering with molecular associations can comprise interfering with the association of the RNA comprising the $r(CUG)^{exp}$ segment and muscleblind-like 1 protein MBL1. For example, interfering with molecular associations can comprise interfering with the association of the RNA comprising the $r(CGG)^{exp}$ segment and DiGeorge Syndrome Critical Region 8 protein (DGCR8), or Src-associated in mitosis, 68 kDa protein (Sam68). It has been found by the inventors herein that formation of a covalent bond between the compound and the RNA provides a significantly higher degree of RNA inactivation compared to contacting the RNA and a compound analogous to the compound but lacking the crosslinking XL group, wherein no covalently-linked complex is formed.

It is believed by the inventors herein that interfering in this manner with the binding of RNA comprising the $r(CUG)^{exp}$ segment and muscleblind-like 1 protein MBL1 will ameliorate the symptoms of DM1 in patients afflicted with this genetically-associated disease. Accordingly, the invention provides, in various embodiments, a method of a treatment of a patient suffering from DM1, comprising administering to the patient an effective dose of the compound of the invention.

It is further believed by the inventors herein that interfering in this manner with the binding of RNA comprising the $r(CGG)^{exp}$ segment and DiGeorge Syndrome Critical Region 8 protein (DGCR8), or Src-associated in mitosis, 68 kDa protein (Sam68), will ameliorate the symptoms of FXTAS in patients afflicted with this genetically-associated disease. Accordingly, the invention provides, in various embodiments, a method of a treatment of a patient suffering from FXTAS, comprising administering to the patient an effective dose of the compound of the invention.

Figure 3:
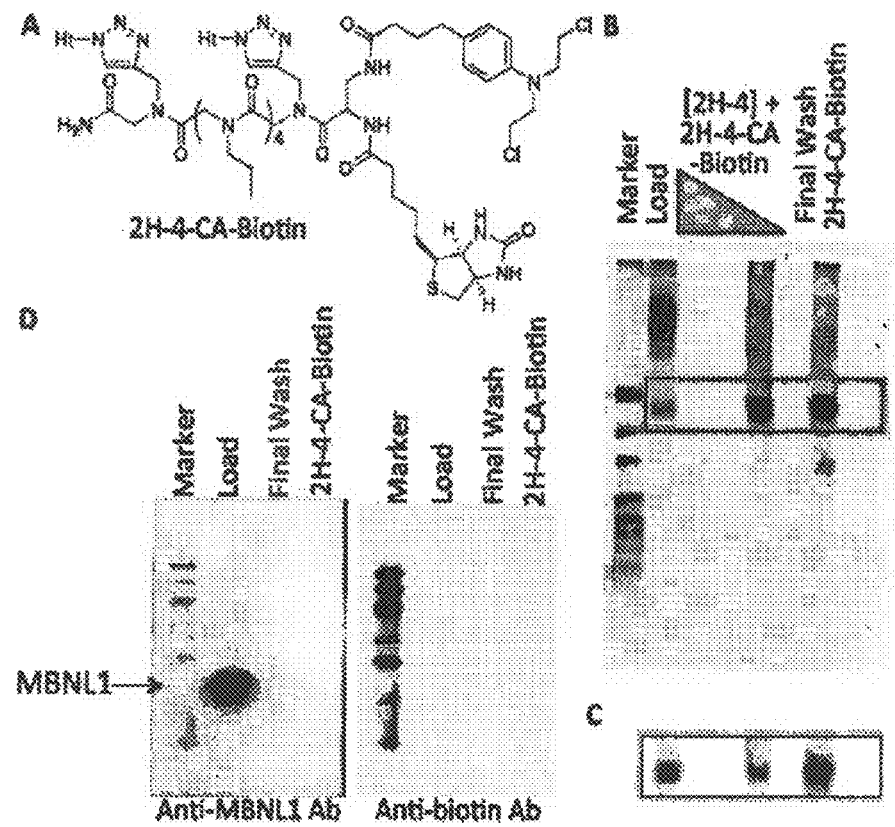
FIG. 3 depicts the structure of 2H-4-CA-Biotin and identification of its cellular targets. A, structure of 2H-4-CA-Biotin; B, gel electrophoresis of nucleic acids captured by 2H-4-CA-Biotin (4 nM) in cells in the presence and absence of competing 2H-4 (10 nM, 1 μM, or 10 μM). The gel was imaged after staining with SYBR Gold. C, northern blot analysis of the gel in B shows that the major target of 2H-4-CA-Biotin is $r(CUG)_{960}$. D, Western blot analysis to determine if MBNL1[11] or other proteins are captured by 2H-4-CA-Biotin (4 nM) in cells. Neither MBNL1 nor other proteins could be detected.
Figure 4:
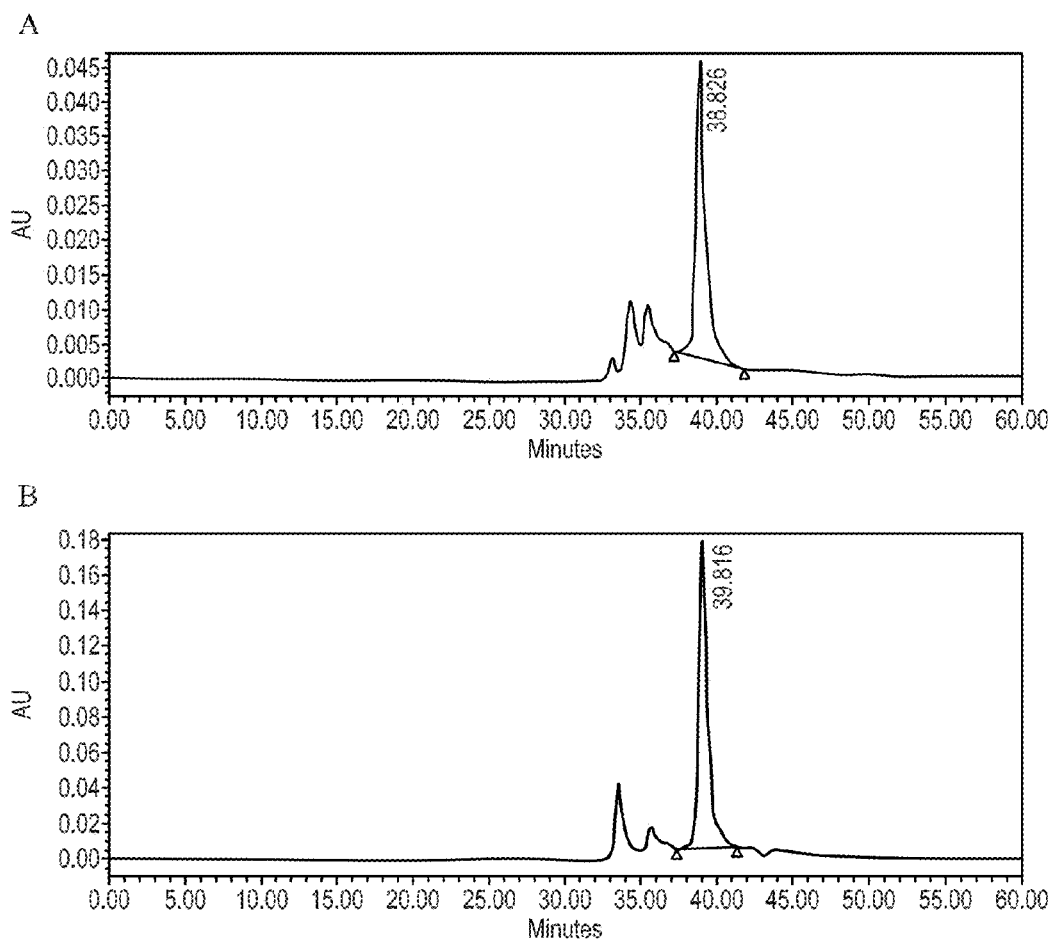
FIG. 4 shows: A, Analytical HPLC trace of 2H-4-CA. The small peaks are hydrolysis products of 2H-4-CA that occurred during lyophilization; B, Analytical HPLC trace of 2H-4-CA-Biotin. The small peaks are hydrolysis products of 2H-4-CA-Biotin that occurred during lyophilization.

In various embodiments, the method described herein provides a method to identify the cellular targets of small molecules directed at RNA. For example, the ability to cross link and form covalent bonds between an RNA and a small molecule that contains an affinity purification tag (e.g., biotin, as in the compound 2H-4-CA-Biotin or 2H-5-CA-Biotin) is described. When one of the aforementioned compounds is added to cell culture, the compound enters cells and reacts with the RNA targets of small molecules. The targets are identified by using various methods including streptavidin resin to capture the biotinylated biomolecules. Biomolecules are analyzed via a variety of methods including gel electrophoresis, northern blots, and RNA sequence (FIG. 3). In a second embodiment of the invention, a method is described to use competition experiments to define the cellular targets of small molecules directed at RNA. For example, as described in FIG. 13, a small molecule that binds to and reacts with RNA targets (2H-4-CA-Biotin or 2H-4-CA-Biotin) can be tested in cells for recognizing targets in the presence of competitor small molecule such as 2H-4. The result is that if, for instance, 2H-4 and 2H-4-CA-Biotin compete for the same cellular target(s) then in the pull down and analysis of targets reacted with 2H-4-CA-Biotin it will be observed that less of the targets that bind 2H-4 will be isolated. The aforementioned competition experiments are useful when the nucleic acid reactive module (e.g., CA) can have non-selective effects for target identification as the competitive assay would identify bonafide targets that are recognized by non-covalent binding.

DOCUMENTS CITED

[1] S. E. Wolkenberg, D. L. Boger, *Chem Rev.* 2002, 102, 2477-2495.

[2] a) K. Rijal, C. S. Chow, *Chem Commun (Camb).* 2009, 107-109.; b) A. A. Hostetter, M. F. Osborn, V. J. DeRose, *ACS Chem. Biol.* 2012, 7, 218-225; c) J. Boer, K. F. Blount, N. W. Luedtke, L. Elson-Schwab, Y. Tor, *Angew. Chem. Int. Ed. Engl.* 2005, 44, 927-932.

[3] a) L. Guan, M. D. Disney, *ACS Chem. Biol.* 2012, 7, 73-86; b) J. R. Thomas, P. J. Hergenrother, *Chem. Rev.* 2008, 108, 1171-1224.

[4] J. Poehlsgaard, S. Douthwaite, *Nat. Rev. Microbiol* 2005, 3, 870-881.

[5] a) J. L. Childs-Disney, M. Wu, A. Pushechnikov, O. Aminova, M. D. Disney, *ACS Chem. Biol.* 2007, 2, 745-754; b) M. D. Disney, L. P. Labuda, D. J. Paul, S. G. Poplawski, A. Pushechnikov, T. Tran, S. P. Velagapudi, M. Wu, J. L. Childs-Disney, *J. Am. Chem. Soc.* 2008, 130, 11185-11194.

[6] a) M. M. Lee, A. Pushechnikov, M. D. Disney, *ACS Chem. Biol.* 2009, 4, 345-355; b) J. L. Childs-Disney, J. Hoskins, S. G. Rzuczek, C. A. Thornton, M. D. Disney, *ACS Chem. Biol.* 2012, 7, 856-862; c) R. Parkesh, J. L. Childs-Disney, M. Nakamori, A. Kumar, E. Wang, T. Wang, J. Hoskins, T. Tran, D. E. Housman, C. A. Thornton, M. D. Disney, *J. Am. Chem. Soc.* 2012, 134, 4731-4742; d) A. Pushechnikov, M. M. Lee, J. L. Childs-Disney, K. Sobczak, J. M. French, C. A. Thornton, M. D. Disney, *J. Am. Chem. Soc.* 2009, 131, 9767-9779. e) Wojciechowska, M.; Krzyzosiak, W. *J. Hum Mol Genet* 2011.

[7] a) H. Jiang, A. Mankodi, M. S. Swanson, R. T. Moxley, C. A. Thornton, *Hum. Mol. Genet.* 2004, 13, 3079-3088; b) N. A. Faustino, T. A. Cooper, *Genes Dev.* 2003, 17, 419-437; c) Day, J. W.; Ranum, L. P. *Neuromuscul Disord* 2005, 15, 5.

[8] a) A. Gellhorn, G. A. Hyman, J. E. Ultmann, *J. Am. Med Assoc.* 1956, 162, 178-183; b) Sellier, C.; Rau, F.; Liu, Y.; Tassone, F.; Hukema, R. K.; Gattoni, R.; Schneider, A.; Richard, S.; Willemsen, R.; Elliott, D. J.; Hagerman, P. J.; Charlet-Berguerand, N. *The EMBO journal* 2010, 29, 1248.

[9] a) C. Z. Chen, K. Sobczak, J. Hoskins, N. Southall, J. J. Marugan, W. Zheng, C. A. Thornton, C. P. Austin, *Anal. Bioanal. Chem.* 2012, 402, 1889-1898; b) Sellier, C.; Freyermuth, F.; Tabet, R.; Tran, T.; He, F.; Ruffenach, F.; Alunni, V.; Moine, H.; Thibault, C.; Page, A.; Tassone, F.; Willemsen, R.; Disney, M. D.; Hagerman, P. J.; Todd, P. K.; Charlet-Berguerand, N. *Cell Rep.* 2013, 3, 869.

[10] a) D. Mohamed, S. Mowaka, J. Thomale, M. W. Linscheid, *Chem. Res. Toxicol.* 2009, 22, 1435-1446; b) S. Kallama, K. Hemminki, *Acta Pharmacol. Toxicol.* 1984, 54, 214-220; c) J. N. Lampe, I. V. Kutyavin, R. Rhinehart, M. W. Reed, R. B. Meyer, H. B. Gamper, Jr., *Nucleic Acids Res.* 1997, 25, 4123-4131 d) Zu, T.; Gibbens, B.; Doty, N. S.; Gomes-Pereira, M.; Huguet, A.; Stone, M.

D.; Margolis, J.; Peterson, M.; Markowski, T. W.; Ingram, M. A.; Nan, Z.; Forster, C.; Low, W. C.; Schoser, B.; Somia, N. V.; Clark, H. B.; Schmechel, S.; Bitterman, P. B.; Gourdon, G.; Swanson, M. S.; Moseley, M.; Ranum, L. P. *Proceedings of the National Academy of Sciences of the United States of America* 2011, 108, 260.

[11] a) I. Holt, S. Mittal, D. Furling, G. S. Butler-Browne, J. D. Brook, G. E. Morris, *Genes Cells* 2007, 12, 1035-1048; b) Todd, P. K.; Oh, S. Y.; Krans, A.; He, F.; Sellier, C.; Frazer, M.; Renoux, A. J.; Chen, K. C.; Scaglione, K. M.; Basrur, V.; Elenitoba-Johnson, K.; Vonsattel, J. P.; Louis, E. D.; Sutton, M. A.; Taylor, J. P.; Mills, R. E.; Charlet-Berguerand, N.; Paulson, H. L. *Neuron.* 2013, 78, 440.

[12] a) D. P. Gates, L. A. Coonrod, J. A. Berglund, *J. Biol. Chem.* 2011, 286, 34224-34233; b) Ash, P. E.; Bienick, K. F.; Gendron, T. F.; Caulfield, T.; Lin, W. L.; Dejesus-Hernandez, M.; van Blitterswijk, M. M.; Jansen-West, K.; Paul, J. W., 3rd; Rademakers, R.; Boylan, K. B.; Dickson, D. W.; Petrucelli, L. *Neuron.* 2013, 77, 639.

[13] a) 2H-4-Pt, a 2H-4 conjugate containing a cis-platin reactive module was synthesized and tested for improving DM1-associated pre-mRNA splicing defects. The compound is inactive. b) Darnell, J. C.; Van Driesche, S. J.; Zhang, C.; Hung, K. Y.; Mele, A.; Fraser, C. E.; Stone, E. F.; Chen, C.; Fak, J. J.; Chi, S. W.; Licatalosi, D. D.; Richter, J. D.; Darnell, R. B. *Cell.* 2011, 146, 247.

[14] a) L. O. Ofori, J. Hoskins, M. Nakamori, C. A. Thornton, B. L. Miller, *Nucleic Acids Res.* 2012, 40, 6380-6390.; b) M. B. Warf M. Nakamori, C. M. Matthys, C. A. Thornton, J. A. Berglund, *Proc. Natl. Acad. Sci. U.S.A.* 2009, 106, 18551-18556 c) *Cell.* 1994, 78, 23.

[15] a) S. P. Jog, S. Paul, W. Dansithong, S. Tring, L. Comai, S. Reddy, *PLoS One* 2012, 7, e48825; b) Sudrik, C.; Arha, M.; Cao, J.; Schaffer, D. V.; Kane, R. S. *Chem Commun (Camb).* 2013, 49, 7457.

[16] L. Guan, M. D. Disney, *Angew. Chem. Int. Ed. Engl.* 2013, 52, 1462-1465; b) Werstuck, G.; Green, M. R. *Science* (New York, N.Y.) 1998, 282, 296.

[17] B. F. Cravatt, A. T. Wright, J. W. Kozarich, *Annu. Rev. Biochem.* 2008, 77, 383-414.

[18] Tran, T.; Childs-Disney, J. L.; Liu, B.; Guan, L.; Rzuczek, S.; Disney, M. D. *ACS Chem Biol* 2014, 9, 904.

EXAMPLES

General The RNA used in the in vitro cleavage assay ($r(CUG)_{10}$) was purchased from Dharmacon and purified as previously described.[e1] Anti-biotin-HRP antibody and the biotinylated protein ladder were purchased from Cell Signaling Technology, Inc. Mouse anti-MBNL1 antibody was obtained from Wolfson Centre for Inherited Neuromuscular Disease.[e2] The DNA primers used for RT-PCR were purchased from Integrated DNA Technologies, Inc. (IDT). Gel images were acquired using a Molecular Dynamics Typhoon Phosphorimager and quantified with QuantityOne version 4.6.5 software. Mass spectra were collected on an ABI 4800 MALDI-TOF spectrometer.

Pull-down of the cellular targets of 2H-5-CA-Biotin and 2P-5-CA-Biotin. COS7 cells were grown in growth medium (1×DMEM, 10% FBS, and 1× GlutaMax (Invitrogen)) as monolayers in a 75 cm² flask to approximately 95% confluency. The cells were transfected with gene of interest (($CGG)_{88}$-GFP or GFP) using Lipofectamine 2000 (Invitrogen) per the manufacturer's recommended protocol. The compound of interest was added to the transfection cocktail (500 nM of final concentration), which was then applied to the cells. After 5 h incubation, the transfection cocktail was removed and replaced with the growth medium containing 500 nM of compound. The cells were then incubated at 37° C. for 18-20 h. Total RNA was extracted by using Trizol reagent (Ambion) according to the manufacturer's protocol. After DNase (Promega) treatment according to the manufacturer's protocol, total RNAs were phenol:chloroform extracted and EtOH precipitated. 100 µg of total RNA was incubated with streptavidin beads (100 µL, Sigma-Aldrich) in 1×PBS (pH 7.4) for 2 h at room temperature with gentle shaking. The solution was removed, and the beads were washed with 5×200 µL $H_2O$ for 5 min each, until the presence of RNA was no longer detected in the wash solution as determined by absorbance at 260 and 280 nm using a Thermo Scientific Nanodrop 2000C spectrophotometer. Bound RNA was released from the beads by heating the beads in 1× Elution Buffer (100 µL, 95% formamide, 10 mM EDTA, pH 8.2) at 65° C. for 5 min. The released RNA was purified by a GenElute™ Mammalian Total RNA Miniprep kit (Sigma-Aldrich) and cDNA was generated from 50 ng of RNA using a qScript cDNA Synthesis Kit (Quanta Biosciences) per the manufacturer's protocol. qPCR was performed on an ABI 7900 HT Real-Time PCR System (Applied Biosystems). Primer sequences for GFP mRNA (GFP-F/R) are provided in Table S1.

MS analysis of the 2H-5-CA-Biotin-$r(CGG)_{60}$ adduct. The RNA $r(CGG)_{60}$ was produced by run-off transcription with T7 RNA polymerase. The RNA (10 pmol, 1 mM) was folded in 1×PBS (pH 7.4) as described above and incubated with 2H-5-CA-Biotin (1 nmol, 100 µM) in a total volume of 10 µL at room temperature for 24 h. The resulting products were digested with nuclease P1 (1 unit) at 37° C. for 16 h. The solution was then diluted to 50 µL and incubated with streptavidin beads (50 µL, Sigma-Aldrich) in 1×PBS (pH 7.4) for 1 h at room temperature with gentle shaking. The solution was removed, and the beads were washed with 5×200 µL $H_2O$ for 5 min each. Bound adduct was released from beads by heating in 1× Elution Buffer at 65° C. for 5 min. The eluate was concentrated under reduced pressure and analyzed using MALDI-TOF mass spectrometry.

Improvement of pre-mRNA splicing defects in a FXTAS cell culture model using RT-PCR. Improvement of pre-mRNA splicing defects by various compounds was tested in cellulo as previously described with minor modifications.[e1] Briefly, COS7 cells were grown as monolayers in 96-well plates in growth medium (1×DMEM, 10% FBS, and 1× GlutaMax (Invitrogen)). After the cells reached 90-95% confluency, they were transfected with 200 ng of total plasmid (150 ng of a plasmid encoding $r(CGG)_{60}$ and 50 ng of the SMN2 mini-gene[e2]) using Lipofectamine 2000 (Invitrogen) per the manufacturer's standard protocol. The compound of interest was added to the transfection cocktail, which was then applied to the cells. Approximately 5 h post-transfection, the transfection cocktail was removed and replaced with growth medium containing the compound, and the cells were incubated at 37° C. for 18-20 h. Total RNA was harvested by lysing the cells in the plate and by using a Quick-RNA™ MiniPrep Kit (Zymo Research). An on-column DNA digestion was completed per the manufacturer's recommended protocol. A sample of RNA was subjected to RT-PCR as previously described,[e1] and the pre-mRNA splicing products were separated by polyacrylamide gel electrophoresis. The primer sequences for the SMN2 mini-gene (SMN2-F/R) are provided in Table S1.

Quantifying RAN and normal translation products by Western blot. COS7 cells were transfected and treated with compound as described above except a plasmid encoding (CGG)$_{88}$-GFP$^{e3}$ was employed. Cells were lysed in the plate using 100 µL/well of MPER Mammalian Protein Extraction Reagent (Pierce Biotechnology) containing 1 µL of Halt Protease Inhibitor cocktail (Thermo Scientific). Cellular proteins were separated by SDS-PAGE and then transferred to a PVDF membrane by wet transfer method. Western blotting was completed using anti-GFP (Santa cruz) or anti-β-actin (Sigma Aldrich) as primary antibodies and anti-IgG-horseradish peroxidase conjugate as the secondary antibody. Chemiluminescent signal was generated by Super-Signal West Pico Chemiluminescent substrate (Thermo Scientific), and the blot was imaged using X-ray film.

Determination of (CGG)$_{88}$-GFP mRNA expression levels by qRT-PCR. COS7 cells were transfected with (CGG)$_{88}$-GFP and treated with compound followed by isolation of total RNA as described above. qRT-PCR was completed as described above. Primer pairs for (CGG)$_{88}$-GFP (GFP-F/R) and β-actin internal control (hACTBF and hACTBR) are provided in Table S. The amounts of the (CGG)$_{88}$-GFP mRNA were normalized to β-actin.

Synthesis of 2H-4-CA and 2P-4-CA (Schemes S1 & S2).

The peptoid scaffold, 2P-4, was synthesized as previously described on Rink amide resin.$^{e3}$ To the 2P-4 resin (100 mg) was added Fmoc-Gly-OH (0.5 M in 1 mL DMF containing 0.5 M HOBT and 0.5 M HBTU) followed by DIPEA (0.2 mL). The reaction was incubated overnight at 37° C. with shaking. The solution was removed, and the resin was washed with DMF (3×5 mL) to afford resin-bound 2P-4-Fmoc-Gly. Ht-N$_3$ (synthesized as previously described)$^{e3}$ (61 µmol, 5 eq.) was then incubated with the resin to afford 2H-4-Fmoc-Gly via a click reaction as previously described.$^{e1,e4}$ The Fmoc-protecting group was removed by treating the resin with 20% piperidine in DMF. 2H-4-Gly was cleaved from the resin using a solution of 95% (v/v) trifluoroacetic acid (TFA), 2.5% (v/v) H$_2$O, and 2.5% (v/v) diisopropylsilane. The solvent was removed under air, and the product (2H-4-Gly) was purified on a Waters 1525 binary HPLC pump equipped with a Waters 2487 dual absorbance detector system. Product was eluted using a linear gradient starting from 80% solvent A (H$_2$O+0.1% (v/v) TFA) and 20% solvent B (MeOH+0.1% (v/v) TFA) to 100% B over 60 min and a flow rate of 5 mL/min.

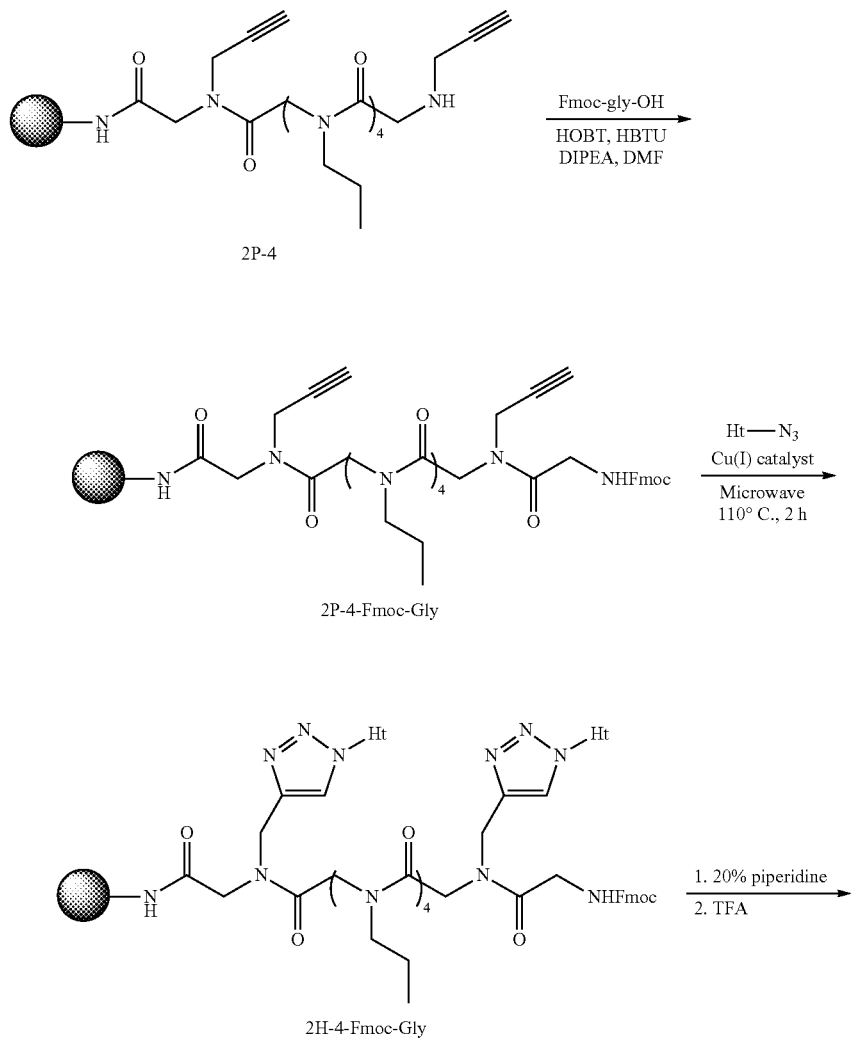

Scheme S1: Synthetic scheme for 2H-4-CA.

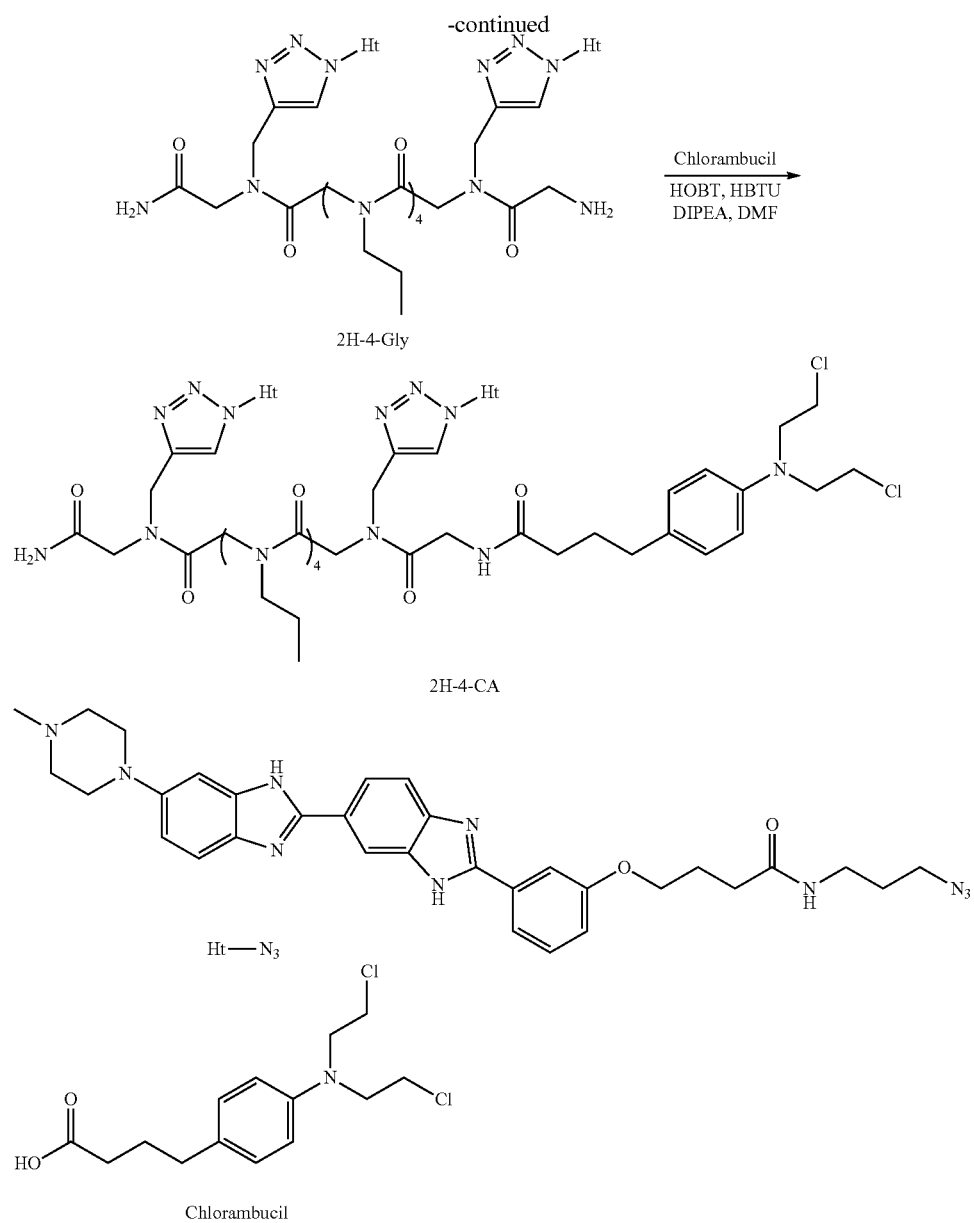
Scheme S2: Synthetic scheme for 2P-4-CA
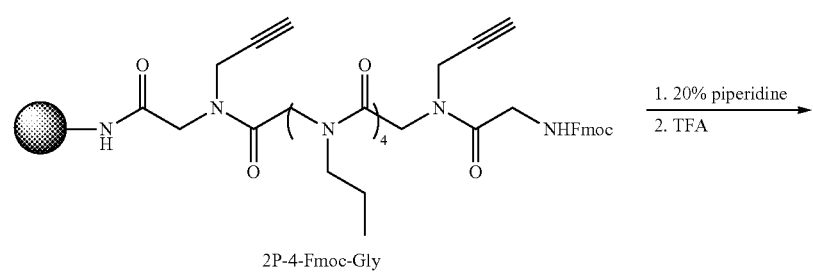
2P-4-Fmoc-Gly

-continued
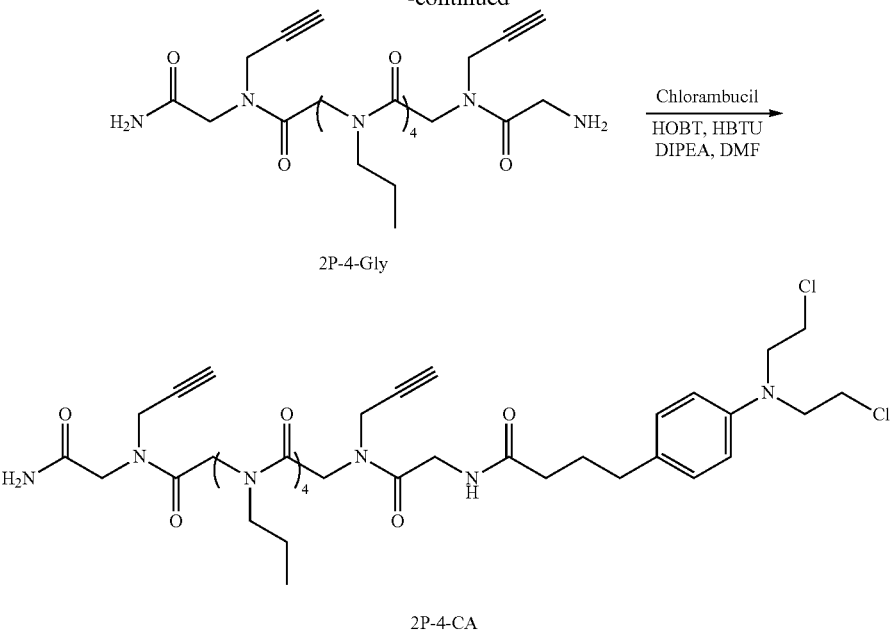
2P-4-Gly
2P-4-CA
Scheme S3: Synthetic scheme for 2H-4-CA-Biotin.
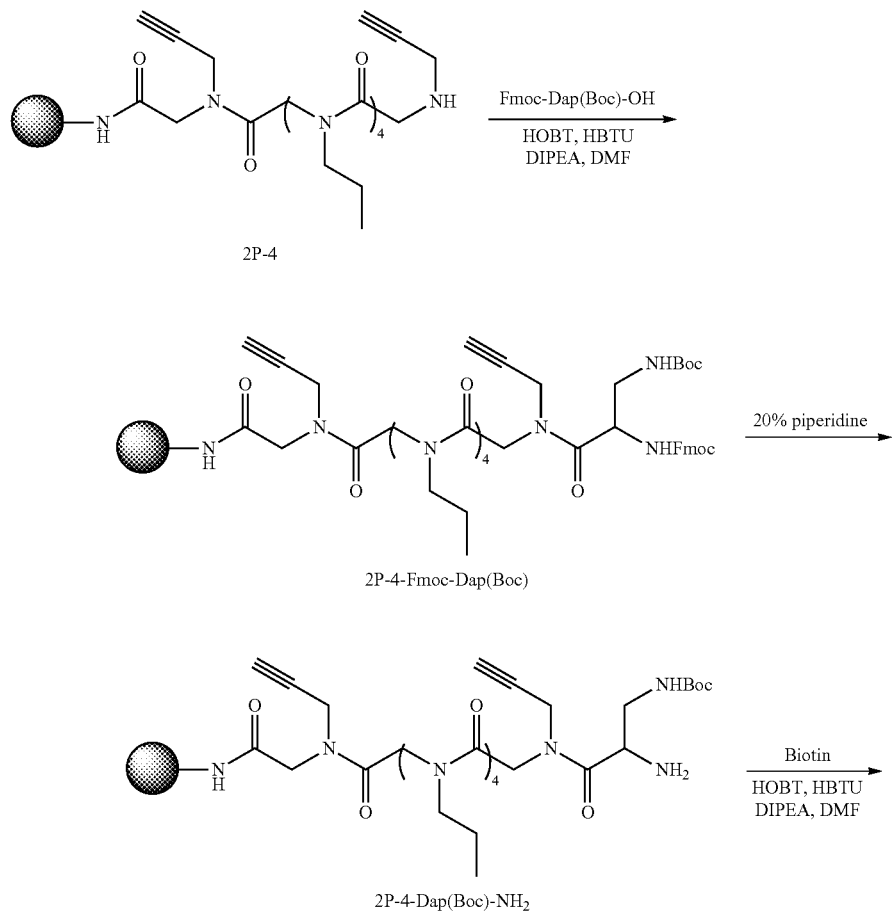
2P-4
2P-4-Fmoc-Dap(Boc)
2P-4-Dap(Boc)-NH$_2$

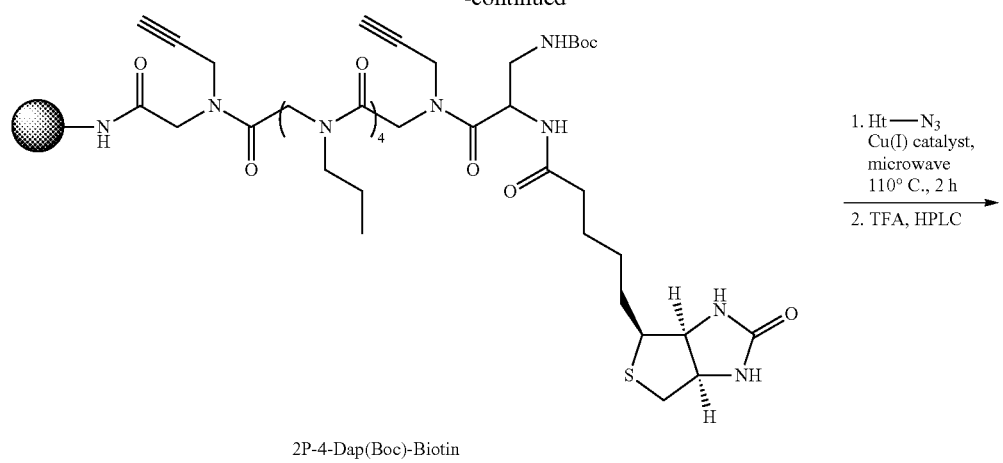
2P-4-Dap(Boc)-Biotin
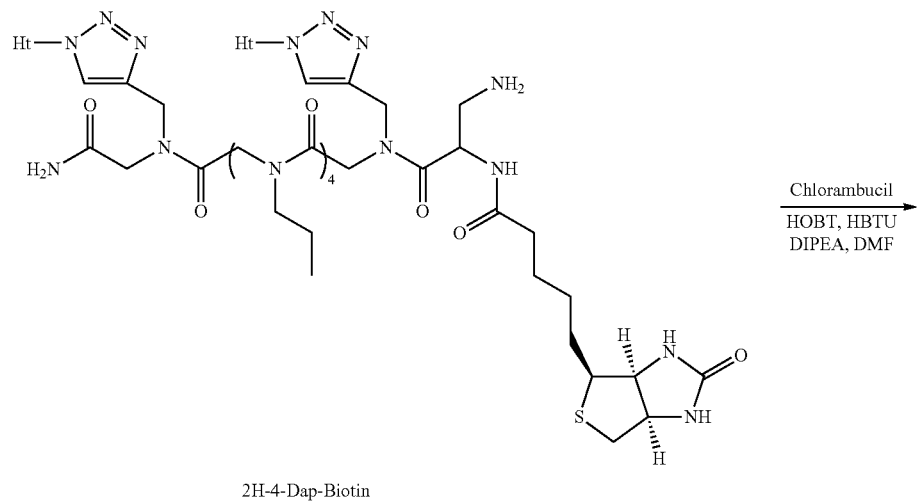
2H-4-Dap-Biotin
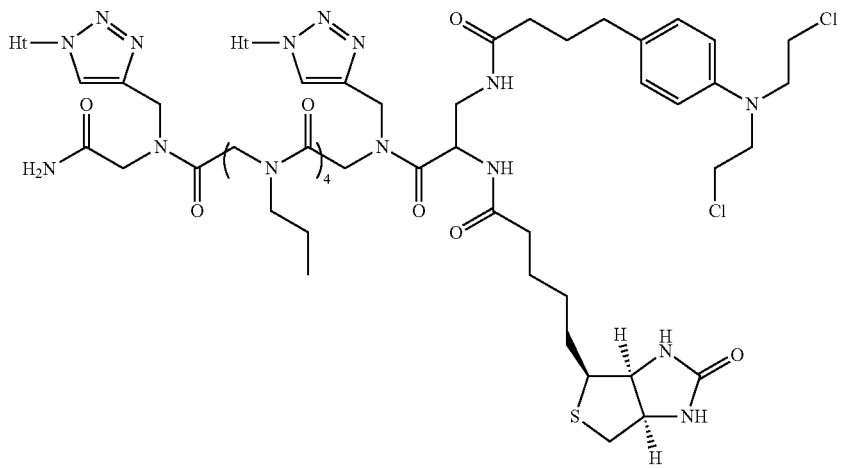
2H-4-CA-Biotin Scheme S4: Synthetic scheme for 2H-4-Pt.

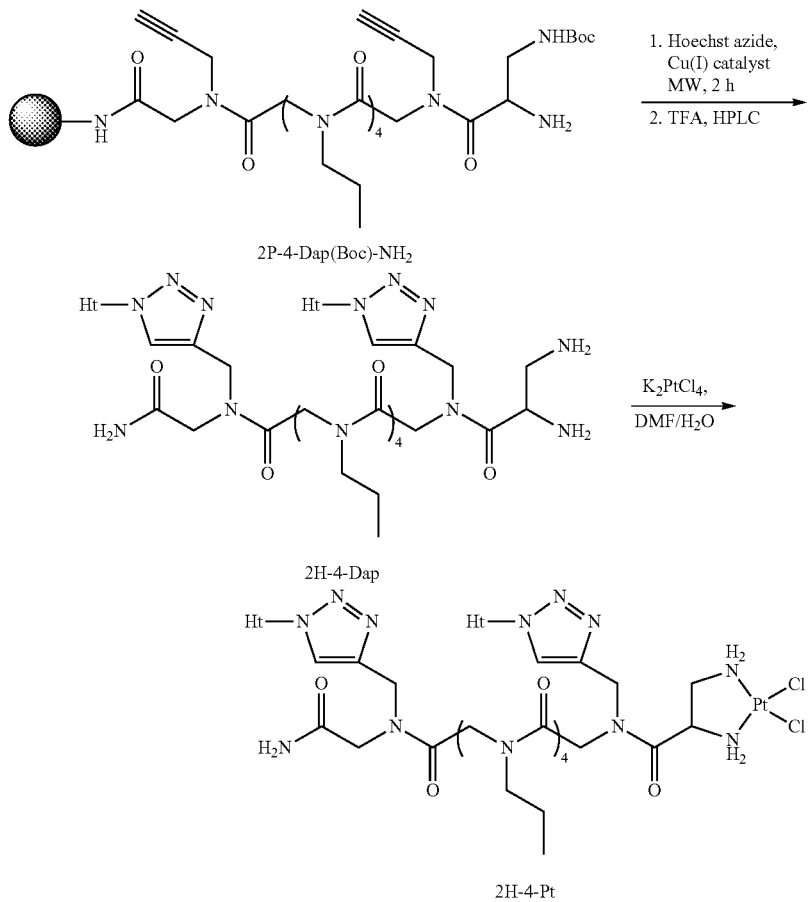

To 2H-4-Gly (75 nmol) in dry DMF (0.025 mL) was added chlorambucil (150 nmol in 1.5 µL DMF) followed by HOBT and HBTU (300 nmol each in 6 µL DMF; 4 eq.) and DIPEA (5 µL). The reaction solution was allowed to stir at room temperature overnight. The product (2H-4-CA) was directly purified by HPLC using the method described above. Yield: 92%; $t_R$: 38.8 (min); MALDI-TOF MS (m/z): calculated: 2132.4; observed: 2133.1.

The 2P-4-CA peptoid was synthesized as described above using 2P-4-Fmoc-Gly (Scheme S2). Yield: 34%; $t_R$: 52.2 (min); MALDI-TOF MS (m/z): calculated: 945.5; observed: 968.6 (M+Na$^+$).

Synthesis of 2H-4-CA-Biotin (Scheme S3). The 2P-4 peptoid was synthesized as described above. To the 2P-4 resin (100 mg) was added Fmoc-Dap(Boc)-OH (0.5 M in 1 mL DMF containing 0.5 M HOBT and 0.5 M HBTU) followed by DIPEA (0.2 mL). The reaction was shaken overnight at 37° C. The solution was removed, and the resin was washed with DMF (3×5 mL), affording resin-bound 2P-4-Fmoc-Dap(Boc). The Fmoc-protecting group was removed by treating the resin with 20% piperidine in DMF at room temperature for 20 min, affording 2P-4-Dap(Boc)-NH$_2$. To the 2P-4-Dap(Boc)-NH$_2$-containing resin was added biotin (0.2 mmol in 1 mL DMF (3.3 eq.) containing 0.3 mmol HOBT and 0.3 mmol HBTU) followed by DIPEA (0.2 mL). The reaction was shaken at 37° C. for 4 h to afford 2P-4-Dap(Boc)-Biotin (resin-bound). Ht-N$_3$ was then clicked with 2P-4-Dap(Boc) as previously described to produce 2H-4-Dap(Boc)-Biotin.[e1,e4] 2H-4-Dap(Boc)-Biotin was de-protected and cleaved from resin using a solution of 95% TFA (v/v), 2.5% (v/v) H$_2$O and 2.5% (v/v) diisopropylsilane. The solvent was removed under a stream of air, and the product (2H-4-Dap-Biotin) was purified by HPLC as described above.

To 2H-4-Dap-Biotin (3 mM) in dry DMF (25 µL) was added chlorambucil (1.5 µL of 100 mM in DMF) followed by HOBT and HBTU (6 µL of 100 mM in DMF) and DIPEA (5 µL). The reaction solution was stirred overnight at room temperature. The product (2H-4-CA-Biotin) was directly purified by HPLC as described above. Yield: 75%; $t_R$: 39.0 min; MALDI-TOF MS (m/z): calculated: 2387.7; observed: 2388.3 (M).

Synthesis of 2H-4-Pt. Ht-N$_3$ (31 µmol; 5 eq.) was clicked to resin-bound 2P-4-Dap(Boc) (synthesized as described above) as previously described to afford 2H-4-Dap(Boc).[e1,e4] 2H-4-Dap(Boc) was de-protected and cleaved from resin using a solution of 95% (v/v) TFA, 2.5% (v/v) H$_2$O and 2.5% (v/v) diisopropylsilane. The solvent was removed under a stream of air, and the product (2H-4-Dap) was purified by HPLC as described above. To 2H-4-Dap (250 nmol) in DMF (0.025 mL) was added potassium tetrachloroplatinate(II) (300 nmol in 3 µL H$_2$O; 1.2 eq.).[e5] The reaction solution was stirred at room temperature overnight. The product (2H-4-Pt) was directly purified by HPLC as described above. Yield: 21%; $t_R$: 34.4 min; MALDI-TOF MS (m/z): calculated: 2139.2; observed: 2141.8 (M+H⁺; multiple peaks due to Pt isotopes. The mass of $^{196}$Pt was reported.

In vitro adduct formation of r(CUG)$_{10}$ with 2H-4-CA. r(CUG)$_{10}$ was 5' end labeled using standard methods (T4 polynucleotide kinase (New England Biolabs) and γ-$^{32}$P-ATP (Perkin Elmer)).[e6] The RNA (50 nM) was folded in 1×PBS (pH 7.4) by heating at 60° C. for 5 min followed by slowly cooling to room temperature on the benchtop. Then, 2H-4-CA, 2H-4-CA-Biotin, or chlorambucil was added, and the sample was incubated at room temperature for 4 h. An aliquot (1 μL) of the reaction solution was mixed with formamide loading buffer (5 μL), and the products were resolved by electrophoresis using a denaturing 20% polyacrylamide gel.

MS analysis of the 2H-4-CA-Biotin-r(CUG)$_{10}$ adduct. r(CUG)$_{10}$ (10 pmol, 1 μM) was folded in 1×PBS (pH 7.4) as described above and incubated with 2H-4-CA-Biotin (1 nmol, 100 μM) in a total volume of 10 μL at room temperature for 22 h. The resulting products were digested with nuclease P1 (1 unit) at 37° C. for 16 h. The solution was then diluted to 50 μL and incubated with streptavidin beads (50 μL, Sigma-Aldrich) in 1×PBS (pH 7.4) for 1 h at room temperature with gentle shaking. The solution was removed, and the beads were washed with 5×200 μL H$_2$O for 5 min each. Bound adduct was released from beads by heating the beads in 1× Elution Buffer (50 μL, 95% formamide, 10 mM EDTA, pH 8.2) at 65° C. for 5 min and analyzed using MALDI-TOF mass spectrometry.

RNase T1 digestion to detect adduct formation between 2H-4-CA and r(CUG)$_{10}$. RNA was 5' end labeled using [γ-$^{32}$P] ATP and prepared as described above. It was then incubated with various concentrations of 2H-4-CA (100, 80, 50, 25, 10, 1, 0.5, 0.1 μM) in 1×PBS (pH 7.4) at room temperature for 22 h. The resulting products were digested with RNase T1 in 1×PBS (pH 7.4) supplemented with 7 M urea at room temperature for 15 min. The cleavage products were resolved by electrophoresis using a denaturing 20% polyacrylamide gel.

Quantitative time-resolved fluorescence resonance energy transfer (qTR-FRET) assay. The qTR-FRET assay used to measure the small molecule's ability to inhibit the r(CUG)$_{10}$-MBNL1 complex (IC$_{50}$'s) was described previously and used with minor modifications. Briefly, 5'-biotinylated r(CUG)$_{10}$ was folded in 1× Folding Buffer (20 mM HEPES, pH 7.5, 110 mM KCl, and 10 mM NaCl) by heating at 60° C. followed by slowly cooling to room temperature on the benchtop. The RNA was Incubated with various concentrations of small molecule (0.5, 1, 5, 10, 25, 50, 100, 150 μM) at room temperature for 4 h or at 37° C. for 20 h. The buffer was adjusted to 1× Assay Buffer (20 mM HEPES, pH 7.5, 110 mM KCl, 10 mM NaCl, 2 mM MgCl$_2$, 2 mM CaCl$_2$, 5 mM dithiothreitol, 0.1% bovine serum albumin (BSA), and 0.5% Tween-20), and MBNL1-His$_6$ was added. The final concentrations of RNA and MBNL1 were 80 nM and 60 nM, respectively. The samples were incubated at room temperature for 15 min. Streptavidin-XL665 (cisbio Bioassays) and anti-His$_6$-Tb (cisbio Bioassays) were added to final concentrations of 40 nM and 0.44 ng/μL, respectively, in a total of volume of 10 μL. Samples were incubated for 1 h at room temperature and then transferred to a well of a white 384-well plate. Time-resolved fluorescence was measured on a Molecular Devices SpectraMax M5 plate reader, and the IC$_{50}$ was determined by curve fitting (4-parameter logistic curve fit) as previously described.[e7]

In vitro reaction of MBNL1 with 2H-4-CA and Western blotting. MBNL1-His$_6$ (177 nM) was incubated with 2H-4-CA-Biotin (100, 50, 10, 1, and 0.1 μM) at room temperature for 22 h. An aliquot (5 μL) of the reaction was resolved by electrophoresis using a 10% SDS-PAGE gel and transferred to PVDF membranes (Gelman Laboratory). After blocking with 1×PBST supplemented with 5% BSA, the membranes were incubated with the appropriate antibodies (MB1a, Clone No. 4A8[e2] or anti-biotin-HRP) for 1 h at room temperature or overnight at 4° C. After incubation, the membranes were washed with 1×PBST. Blots probed with anti-MBNL1 were then incubated with goat anti-Mouse IgG-HRP (Thermo Fisher Scientific, Inc.). Protein was detected by using SuperSignal West Pico Chemiluminescent Substrates (Thermo Fisher Scientific Inc.) according to the manufacturer's protocol.

Improvement of pre-mRNA splicing defects in a DM1 cell culture model using RT-PCR. Improvement of pre-mRNA splicing defects by various compounds was tested in vivo as previously described.[e1] Briefly, HeLa cells were grown as monolayers in 96-well plates in growth medium (1×DMEM, 10% FBS, and 1× GlutaMax (Invitrogen)). After the cells reached 90-95% confluence, they were transfected with 200 ng of total plasmid using Lipofectamine 2000 reagent (Invitrogen) per the manufacturer's standard protocol. Equal amounts of a plasmid expressing a DM1 mini-gene with 960 CTG repeats and a mini-gene of interest (modified bichromatic reporter (RG6 or PLEKHH2) were used. Approximately 5 h post-transfection, the transfection cocktail was removed and replaced with growth medium containing the compound of interest. The cells were then incubated at 37° C. for 20-24 h. Total RNA was harvested by lysing the cells in the plate and by using a GenElute™ Mammalian Total RNA Miniprep Kit (Sigma-Aldrich). An on-column DNA digestion was completed per the manufacturer's recommended protocol. A sample of RNA was subjected to RT-PCR as previously described, and RT-PCR products were separated by PAGE. The primer sequences for both mini-genes are provided in Table S1.

Determination of DMPK mRNA expression levels in a DM1 cell culture model by real time RT-PCR. HeLa cells were transfected and treated with compounds followed by isolation of total RNA as described above. cDNA was generated from 150 ng of RNA as previously described. Power SYBR® Green PCR Master Mix (Applied Biosystems) was used to quantify the amount of DMPK mRNA (contains r(CUG)$_{960}$) per the manufacturer's protocol. Primer pairs that are upstream of DMPK exon 15 containing r(CUG)$_{960}$ mRNA (E15upF and E15upR) and a β-actin internal control (hACTBF and hACTBR) were used (Table S1). qPCR was performed on an ABI 7900 HT Real-Time PCR System. The amount of the r(CUG)$_{960}$-containing DMPK mRNA was normalized relative to β-actin.

Pull-down of the cellular targets of 2H-4-CA-Biotin and Northern blotting. HeLa cells were grown as monolayers in a 75 cm² flask to approximately 95% confluence. The cells were transfected with a plasmid expressing a DM1 mini-gene using Lipofectamine 2000 (Invitrogen) per the manufacturer's recommended protocol and treated with compound as described above. After cells were incubated at 37° C. for 20-24 h, the growth medium containing compound was removed and the cells were washed with 1×DPBS. Total RNA was extracted by using TRIzol reagent (Ambion) according to the manufacturer's protocol. Approximately 200 μg of total RNA was incubated with streptavidin beads (100 μL, Sigma-Aldrich) in 1×PBS (pH 7.4) for 1 h at room temperature with gentle shaking. The solution was removed, and the beads were washed with 5×200 μL of 1×TBST (pH 7.4), followed by 5×200 μL H$_2$O for 5 min each. The presence of RNA in the wash solution was no longer detected as determined by absorbance at 260 and 280 nm using a Thermo Scientific Nanodrop 2000C spectrophotometer. Bound RNA was released by heating the beads in 1× Elution Buffer (50 µL, 95% formamide, 10 mM EDTA, pH 8.2) at 65° C. for 5 min.

The above RNA samples (5 µg) were separated on 1.25% (w/v) agarose gel containing 6.66% (v/v) formaldehyde. The gel was then stained with ethidium bromide or 1×SYBR gold (Invitrogen) in 0.5×TBE buffer for 30 min. Stained gels were imaged with a Molecular Dynamics Typhoon 9410 variable mode imager. The RNA was then transferred to a nylon membrane (Hybond N+, Amersham). The DMPK mRNA containing r(CUG)$^{exp}$ was probed with $^{32}$P-labeled d(CAG)$_{10}$ and the 18S ribosomal RNA was probed with a complementary, $^{32}$P-labeled oligonucleotide (18S-R, Table S1). The blot was imaged using a Molecular Dynamics Typhoon 9410 variable mode imager.

Pull-down of the protein targets of 2H-4-CA and Western blotting. HeLa cells were grown as monolayers in a 75 cm$^2$ flask to approximately 95% confluence. The cells were transfected with a plasmid expressing a DM1 mini-gene using Lipofectamine 2000 (Invitrogen) per the manufacturer's recommended protocol and treated with compound as described above. Total protein was extracted by using M-PER Mammalian Protein Extraction Reagent (Pierce Biotechnology) according to the manufacturer's protocol.

Approximately 1 mg of total protein was incubated with streptavidin beads (100 µL, Sigma-Aldrich) in 1×PBS (pH 7.4) for 1 h at room temperature with gentle shaking. The solution was removed, and the beads were washed with 5×200 µL of 1×TBST (pH 7.4), followed by 5×200 µL H$_2$O for 5 min each. Bound protein was released from the beads by heating in 1× Elution Buffer (50 µL, 95% formamide, 10 mM EDTA, pH 8.2) at 65° C. for 5 min. Western blotting of the samples using 20 µg of total protein was completed as described above.

Synthesis of 2H-5-CA-Biotin and 2P-5-CA-Biotin (Scheme S5).

2H-5-CA-Biotin was synthesized as described previously.[e16] The peptoid scaffold, 2P-5, was synthesized as previously described on Rink amide resin.[e16] To the 2P-5 resin (100 mg, 0.059 mmoles) was added a mixture of Fmoc-Dap (Boc)-OH (0.59 mmoles), HOBT (0.59 mmoles), HBTU (0.59 mmoles), and DIPEA (0.3 mL) in 2 mL of DMF. The reaction was incubated overnight at 37° C. with shaking. The solution was removed and the resin was washed with DMF (3×5 mL) to afford resin-bound 2P-5-Fmoc-Dap(Boc). The Fmoc-protecting group was removed by treating the resin with 20% piperidine in DMF at room temperature for 20 min, affording 2P-4-Dap(Boc)-NH$_2$. To the 2P-5-Dap (Boc)-NH$_2$-containing resin was added biotin (0.2 mmol, 3.3 eq.), 0.3 mmol HOBT, and 0.3 mmol HBTU, and DIPEA (0.3 mL) dissolved in 2 mL of DMF. The reaction was shaken at 37° C. for 4 h to afford 2P-5-Dap(Boc)-Biotin (resin-bound). After washing the resin with DMF three times, Ht-N$_3$ (synthesized as previously described)[e17] (61 µmol, 5 eq.) in DMF was added to the resin to afford 2H-5-Dap(Boc)-Biotin via a click reaction.[e18,e19] 2H-5-Dap (Boc)-Biotin was cleaved from resin using a solution of 60% (v/v) trifluoroacetic acid (TFA), 30% (v/v) DCM, and 10% (v/v) H$_2$O. The solvent was removed under a stream of air, and the product (2H-5-Dap-Biotin) was purified on a Waters 1525 binary HPLC pump equipped with a Waters 2487 dual absorbance detector system and a SunFire™ Prep C18 OBD™ 5☐5 19×150 mm column. Product was eluted using a linear gradient starting from 80% solvent A (H$_2$O+0.1% (v/v) TFA) and 20% solvent B (MeOH+0.1% (v/v) TFA) to 0% A and 100% B over 60 min and a flow rate of 5 mL/min To 2H-5-Dap-Biotin (1 µmol) in dry DMF (0.1 mL) was added a mixture of chlorambucil (2 µmol), HOBT (8 µmol), HBTU (8 µmol) and DIPEA (5 µL) in 0.12 mL of DMF. The reaction solution was stirred at room temperature overnight. The product (2H-5-CA-Biotin) was directly purified by HPLC using the method described above. yield: 35%; $t_R$: 26 (min); MALDI-TOF MS (m/z): calculated: 2484.2; observed: 2485.2 (M+H).

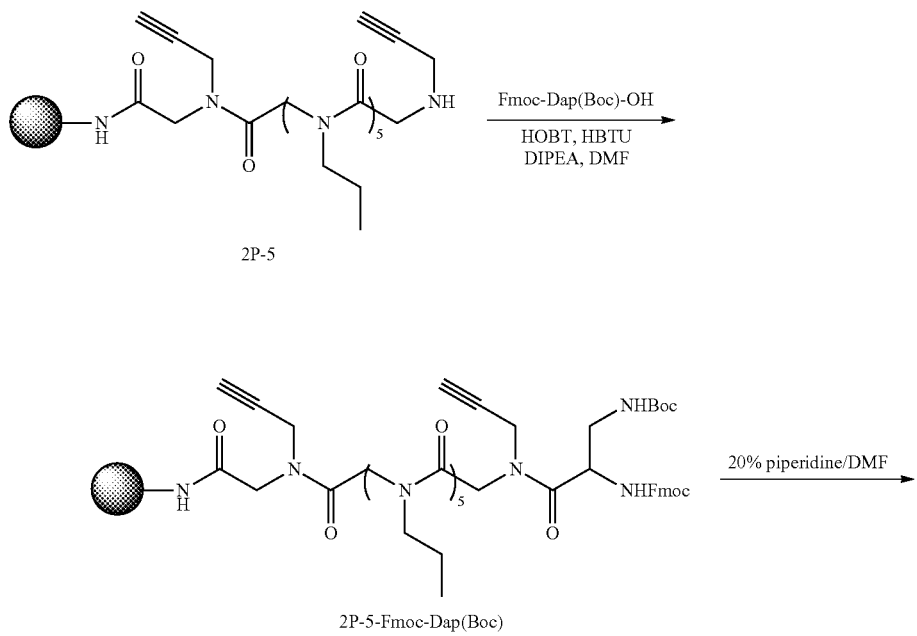

Scheme S5

-continued
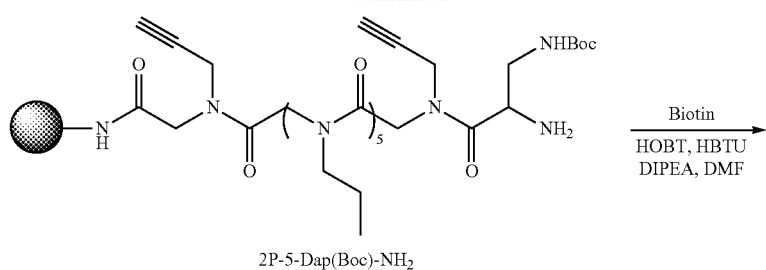
2P-5-Dap(Boc)-NH₂
Biotin
―――――――→
HOBT, HBTU
DIPEA, DMF
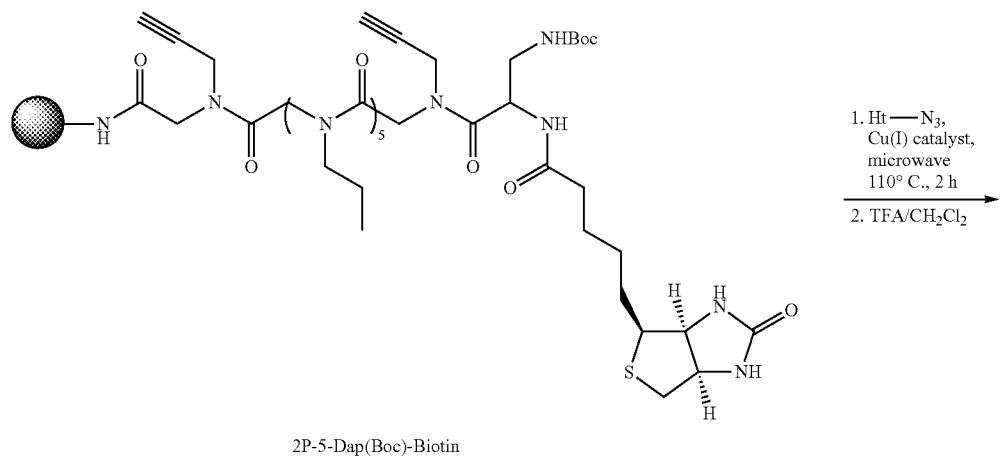
2P-5-Dap(Boc)-Biotin
1. Ht—N₃, Cu(I) catalyst, microwave 110° C., 2 h
2. TFA/CH₂Cl₂
―――――――→
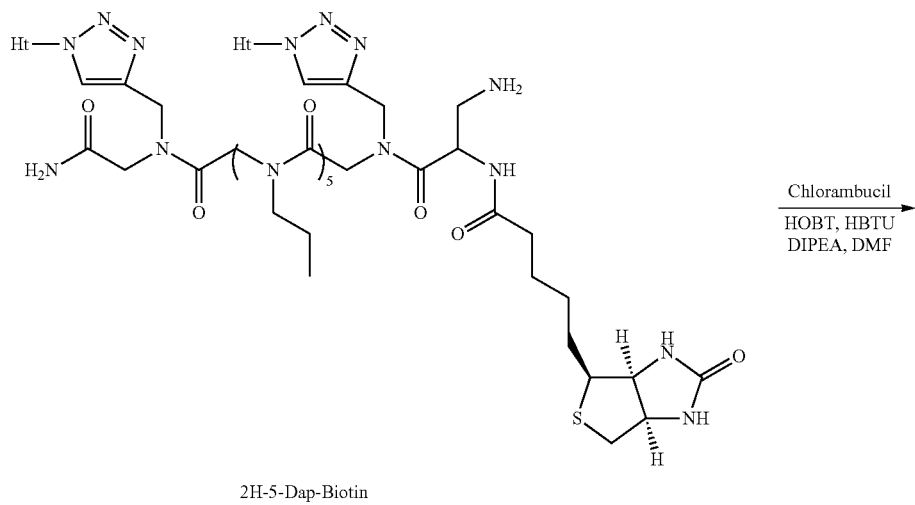
2H-5-Dap-Biotin
Chlorambucil
―――――――→
HOBT, HBTU
DIPEA, DMF 41
42
-continued
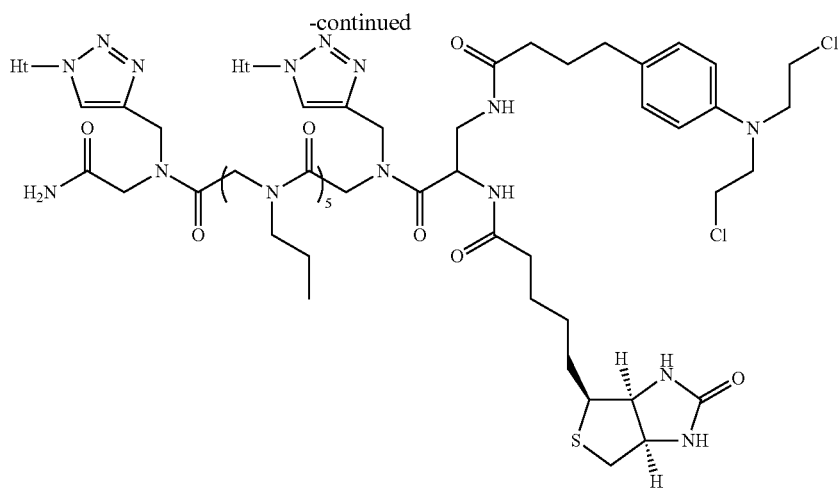
2H-5-CA-Biotin
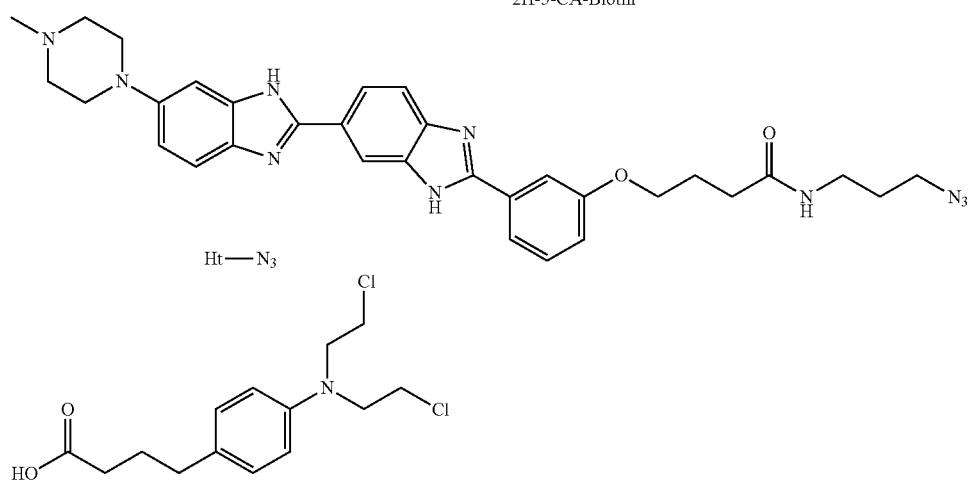
Ht—N₃
Chlorambucil
Scheme S6: Synthetic scheme for 2P-5-CA-Biotin.
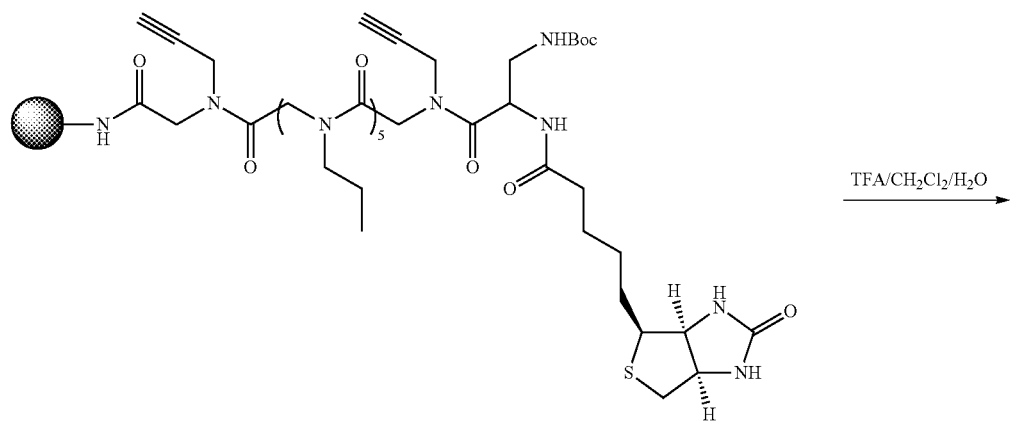
2P-5-Dap(Boc)-Biotin
TFA/CH₂Cl₂/H₂O →

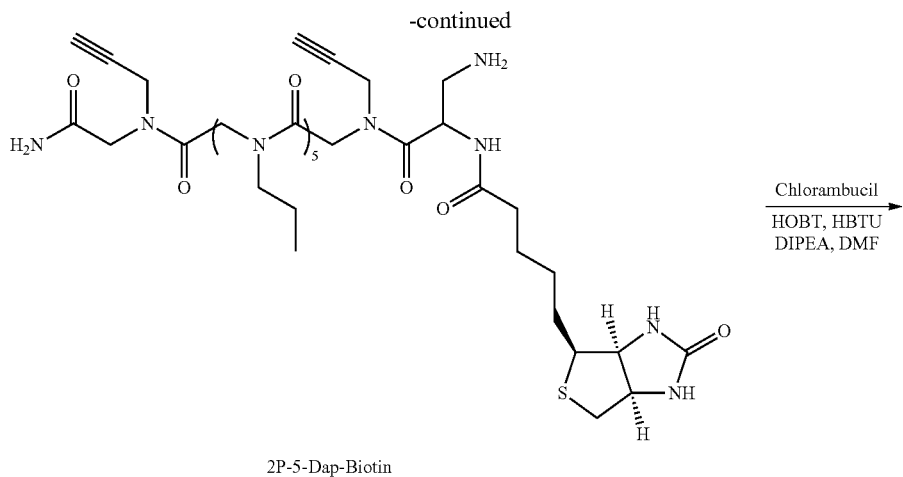

2P-5-Dap-Biotin

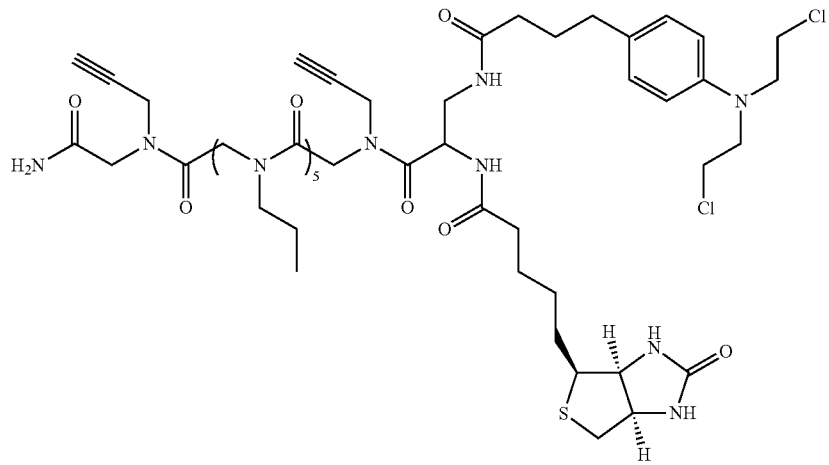

2P-5-CA-Biotin

The 2P-5-CA-Biotin peptoid was synthesized as described above using 2P-5-Dap(Boc)-Biotin (Scheme S6). yield: 40%; $t_R$: 47 (min); MALDI-TOF MS (m/z): calculated: 1299.6; observed: 1322.7 (M+Na$^+$).

Characterization of 2H-5-CA-Biotin and 2P-5-CA-Biotin
The purities of compounds were determined by analytical HPLC using a Waters 1525 Binary HPLC Pump equipped with Waters 2487 Dual λ Absorbance Detector system and the following conditions: a Waters Symmetry® C8 5 μm 4.6×150 mm column, room temperature, a flow rate of 1 mL/min, and a linear gradient of 0% to 100% B in A for 60 min.

Abbreviations

BSA, bovine serum albumin; DCM, dichloromethane; DIPEA, N,N-diisopropylethylamine; DMF, N,N-dimethylformamide; DMPK, dystrophia myotonica protein kinase; DMSO, dimethyl sulfoxide; DPBS, Dulbecco's phosphate-buffered saline; FBS, fetal bovine serum; HBTU, O-(benzotriazol-1-yl)-N,N,N',N'-tetramethyluronium hexafluorophosphate; HEPES, 4-(2-hydroxyethyl)piperazine-1-ethanesulfonic acid; HOBT, 1-hydroxybenzotriazole; HPLC, high performance liquid chromatography; MALDI-TOF, matrix-assisted laser desorption/ionization time-of-flight; MBNL1, muscleblind-like 1 protein; PAGE, polyacrylamide gel electrophoresis; PBS, phosphate buffered saline; PBST, phosphate buffered saline supplemented with 0.1% Tween 20; PLEKHH2, pleckstrin homology domain containing, family H member 2; qPCR, quantitative real time polymerase chain reaction; qTR-FRET, quantitative time-resolved fluorescence resonance energy transfer, RT-PCR, reverse transcription polymerase chain reaction; SDS, sodium dodecyl sulfate; SSC, saline-sodium citrate; TBE, tris-borate-EDTA buffer; TBST, Tris buffered saline supplemented with 0.1% Tween-20; $t_R$, retention time.

TABLE S1

Sequences of the primers used in RT-PCR analyses.

| Primer name | Sequence |
| --- | --- |
| RG-F | 5'-CAA AGT GGA GGA CCC AGT ACC |
| RG-R | 5'-GCG CAT GAA CTC CTT GAT GAC |
| PLEKHH2-F | 5'-CGG GGT ACC AAA TGC TGC AGT TGA CTC TCC |
| PLEKHH2-R | 5'-CCG CTC GAG CCA TTC ATG AAG TGC ACA GG |

TABLE S1-continued

Sequences of the primers used in RT-PCR analyses.

| Primer name | Sequence |
|---|---|
| 18S-F | 5'-GTA ACC CGT TGA ACC CCA TT |
| 18S-R | 5'-CCA TCC AAT CGG TAG TAG CG |
| E15upF | 5'-TCG GAG CGG TTG TGA ACT |
| E15upR | 5'-GTT CGC CGT TGT TCT GTC |
| hACTBF | 5'-CCT GGC ACC CAG CAC AAT |
| hACTBR | 5'-GGG CCG GAC TCG TCA TAC |

"F" indicates a forward primer while "R" indicates a reverse primer

TABLE S2

Potency of 2H-4 and 2H-4-CA for inhibiting r(CUG)$_{10}$-MBNL1 complex formation. The compounds were incubated with the RNA at 37° C. for 22 h.[a]

| Compound | IC$_{50}$ (μM) |
|---|---|
| 2H-4 | 56.4 ± 3.1 |
| 2H-4-CA | 1.8 ± 1.1 |

[a]Experiments were completed by using a previously described time-resolved FRET assay[12] with minor modifications.

TABLE S3

Sequences of the primers used in RT-PCR analyses.

| Primer name | Sequence |
|---|---|
| SMN2-F | 5'-GGT GTC CAC TCC CAG TTC AA |
| SMN2-R | 5'-GCC TCA CCA CCG TGC TGG |
| (CGG)60-F | 5'-GAA CCC ACT GCT TAC TGG CTTA |
| (CGG_60-R | 5'-AAC GCT AGC AGC TTG GGG TC |
| hACTBF | 5'-CCT GGC ACC CAG CAC AAT |
| hACTBR | 5'-GGG CCG GAC TCG TCA TAC |
| GFP-F | 5'-GCA CGA CTT CTT CAA GTC CGC CAT GCC |
| GFP-R | 5'-GCG GAT CTT GAA GTT CAC CTT GAT GCC |

"F" indicates a forward primer while "R" indicates a reverse primer.

DOCUMENTS CITED IN EXAMPLES SECTION e1) J. L. Childs-Disney, J. Hoskins, S. G. Rzuczek, C. A. Thornton, M. D. Disney, *ACS Chem. Biol.* 2012, 7, 856-862.

e2) I. Holt, S. Mittal, D. Furling. G. S. Butler-Browne, J. D. Brook, G. E. Morris, *Genes Cells* 2007, 12, 1035-1048.

e3) A. Pushechnikov, M. M. Lee, J. L. Childs-Disney, K. Sobczak, J. M. French, C. A. Thornton, M. D. Disney, *J. Am. Chem. Soc.* 2009, 131, 9767-9779.

e4) A. Agrawal, C. A. de Oliveira, Y. Cheng, J. A. Jacobsen, J. A. McCammon, S. M. Cohen, *J. Med. Chem.* 2009, 52, 1063-1074.

e5) J. Boer, K. F. Blount, N. W. Luedtke, L. Elson-Schwab, Y. Tor, *Angew. Chem. Int. Ed. Engl.* 2005, 44, 927-932.

e6) J. Sambrook, E. F. Fritsch, T. Maniatis, *Molecular Cloning*, 2nd ed., Cold Spring Harbor Laboratory, Cold Spring Harbor, N.Y., 1989.

e7) R. Parkesh, J. L. Childs-Disney, M. Nakamori, A. Kumar, E. Wang, T. Wang, J. Hoskins, T. Tran, D. Housman, C. A. Thornton, M. D. Disney, *J. Am. Chem. Soc.* 2012, 134, 4731-4742.

e8) A. V. Philips, L. T. Timchenko, T. A. Cooper, *Science* 1998, 280, 737-741.

e9) J. P. Orengo, D. Bundman, T. A. Cooper, *Nucleic Acids Res.* 2006, 34, e148.

e10) M. B. Warf, J. A. Berglund, *RNA* 2007, 13, 2238-2251.

e11) a) J. E. Lee, C. F. Bennett, T. A. Cooper, *Proc. Natl. Acad. Sci. U.S.A.* 2012, 109, 4221-4226; b) J. P. Orengo, P. Chambon, D. Metzger, D. R. Mosier, G. J. Snipes, T. A. Cooper, *Proc. Natl. Acad. Sci. U.S.A* 2008, 105, 2646-2651.

e12) C. Z. Chen, K. Sobczak, J. Hoskins, N. Southall, J. J. Marugan, W. Zheng, C. A. Thornton, C. P. Austin, *Anal. Bioanal. Chem.* 2012, 402, 1889-1898.

e13) Disney, M. D.; Liu, B.; Yang, W.; Sellier, C.; Tran, T.; Charlet-Berguerand, N.; Childs-Disney, J. L. *ACS Chem Biol* 2012, 7, 1711.

e14) Sellier, C.; Rau, F.; Liu, Y.; Tassone, F.; Hukema, R. K.; Gattoni, R.; Schneider, A.; Richard, S.; Willemsen, R.; Elliott, D. J.; Hagerman, P. J.; Charlet-Berguerand, N. *EMBO J* 2010, 29, 1248.

e15) Todd, P. K.; Oh, S. Y.; Krans, A.; He, F.; Sellier, C.; Frazer, M.; Renoux, A. J.; Chen, K. C.; Scaglione, K. M.; Basrur, V.; Elenitoba-Johnson, K.; Vonsattel, J. P.; Louis, E. D.; Sutton, M. A.; Taylor, J. P.; Mills, R. E.; Charlet-Berguerand, N.; Paulson, H. L. *Neuron.* 2013, 78, 440.

e16) Tran, T.; Childs-Disney, J. L.; Liu, B.; Guan, L.; Rzuczek, S.; Disney, M. D. *ACS Chemical Biology* 2014, 9, 904.

e17) Pushechnikov, A.; Lee, M. M.; Childs-Disney, J. L.; Sobczak, K.; French, J. M.; Thornton, C. A.; Disney, M. D. *J Am Chem Soc* 2009, 131, 9767.

e18) Childs-Disney, J. L.; Hoskins, J.; Rzuczek, S. G.; Thornton, C. A.; Disney, M. D. *ACS Chem Biol* 2012, 7, 856.

e19) Agrawal, A.; de Oliveira, C. A.; Cheng. Y.; Jacobsen, J. A.; McCammon, J. A.; Cohen, S. M. *J Med Chem* 2009, 52, 1063.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of identifying an RNA target of a small molecule drug in vivo, comprising contacting a living cell with a small molecule drug conjugate comprising an RNA targeting group, a crosslinking group reactive with the RNA, and an affinity group, then, optionally, activating the crosslinking group, then, separating RNA targets crosslinked to the small molecule drug conjugate by an interaction of the affinity group with a complementary affinity group;

wherein the small molecule drug conjugate is a compound of formula (I)

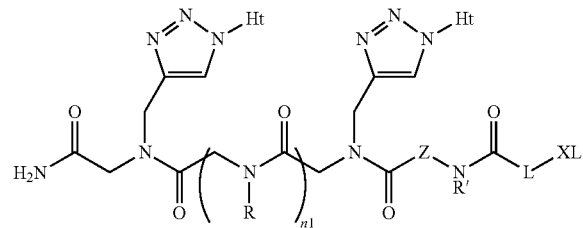

wherein
each individually selected R or R' is H or (C1-C6)alkyl;
n1 is 2, 3, 4, 5, or 6;
Z is a (C1-C3)alkylene group, optionally substituted with a reporter or affinity group;
L is a linker group comprising an optionally substituted (C1-C6)alkylene, wherein one or two carbon atoms is optionally replaced by O;
XL is an RNA-reactive crosslinking group;
each individually selected Ht is an RNA-targeting group;
or any tautomer thereof; or any salt thereof, or any stereoisomer thereof.

2. The method of claim 1 wherein for the compound of formula (I), the crosslinking group is an alkylating group.

3. The method of claim 2 wherein for the compound of formula (I) the alkylating group is a chlorambucil derivative.

4. The method of claim 1 wherein for the compound of formula (I) the crosslinking group is a triggered crosslinker using photochemical or shape-triggered catalysis.

5. The method of claim 1 wherein for the compound of formula (I), Z is an alkylene group substituted with an affinity group.

6. The method of claim 5 wherein the affinity group is a biotin-comprising moiety.

7. The method of claim 1 wherein each individually selected Ht is a group of formula

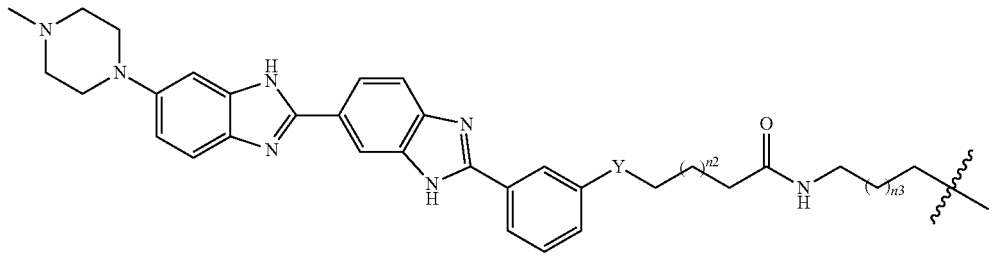

wherein
n2 is 0, 1, 2, or 3;
n3 is 0, 1, 2, or 3;
Y is O or CH$_2$; and,
a wavy line indicates a point of bonding.

* * * * *

UNITED STATES PATENT AND TRADEMARK OFFICE
CERTIFICATE OF CORRECTION

PATENT NO. : 9,933,419 B2
APPLICATION NO. : 15/427288
DATED : April 3, 2018
INVENTOR(S) : Disney et al.

Page 1 of 1

It is certified that error appears in the above-identified patent and that said Letters Patent is hereby corrected as shown below:

In the Specification

Column 1, Line 11, insert the paragraph below:
-- STATEMENT OF GOVERNMENT LICENSE RIGHTS
This invention was made with government support under grant number GM079235 awarded by The National Institutes of Health. The government has certain rights in the invention. --

Signed and Sealed this
First Day of June, 2021

Drew Hirshfeld
*Performing the Functions and Duties of the
Under Secretary of Commerce for Intellectual Property and
Director of the United States Patent and Trademark Office*